US009458174B2

(12) United States Patent
Clement-Schatlo et al.

(10) Patent No.: US 9,458,174 B2
(45) Date of Patent: Oct. 4, 2016

(54) INHIBITORS OF THE ACTIVITY OF COMPLEX (III) OF THE MITOCHONDRIAL ELECTRON TRANSPORT CHAIN AND USE THEREOF

(71) Applicant: STEMERGIE BIOTECHNOLOGY SA, Geneva (CH)

(72) Inventors: Virginie Clement-Schatlo, Suhr (CH); Thomas Fessard, Zürich (CH); Damien Barbaras, Baar (CH); Joana Matos, Zürich (CH); Erick Carreira, Zumikon (CH)

(73) Assignee: Stemergie Biotechnology SA, Geneva (CH)

( * ) Notice: Subject to any disclaimer, the term of this patent is extended or adjusted under 35 U.S.C. 154(b) by 0 days.

(21) Appl. No.: 14/401,685

(22) PCT Filed: May 23, 2013

(86) PCT No.: PCT/EP2013/060670
§ 371 (c)(1),
(2) Date: Nov. 17, 2014

(87) PCT Pub. No.: WO2013/174974
PCT Pub. Date: Nov. 28, 2013

(65) Prior Publication Data
US 2015/0148301 A1  May 28, 2015

(30) Foreign Application Priority Data
May 23, 2012 (CH) ........................................ 0715/12

(51) Int. Cl.
*A61K 31/41* (2006.01)
*C07D 495/10* (2006.01)
(Continued)

(52) U.S. Cl.
CPC ............ *C07D 495/10* (2013.01); *A01N 31/08* (2013.01); *A01N 33/10* (2013.01); *A01N 35/04* (2013.01); *A01N 37/24* (2013.01); *A01N 37/40* (2013.01); *A01N 37/44* (2013.01); *A01N 37/46* (2013.01); *A01N 37/50* (2013.01); *A01N 43/20* (2013.01); *A01N 43/38* (2013.01); *A01N 43/40* (2013.01); *A01N 43/42* (2013.01); *A01N 43/46* (2013.01); *A01N 43/52* (2013.01); *A01N 43/56* (2013.01); *A01N 43/60* (2013.01); *A01N 43/647* (2013.01); *A01N 43/76* (2013.01); *A01N 43/78* (2013.01); *A01N 43/80* (2013.01); *A01N 43/90* (2013.01); *A01N 47/30* (2013.01); *A61K 31/137* (2013.01); *A61K 31/167* (2013.01); *A61K 31/17* (2013.01); *A61K 31/18* (2013.01); *A61K 31/397* (2013.01); *A61K 31/421* (2013.01); *A61K 31/44* (2013.01); *A61K 31/47* (2013.01); *A61K 31/55* (2013.01); *A61K 45/06* (2013.01); *C07C 39/245* (2013.01); *C07C 39/30* (2013.01); *C07C 43/1787* (2013.01); *C07C 49/245* (2013.01); *C07C 49/825* (2013.01); *C07C 215/50* (2013.01); *C07C 233/25* (2013.01); *C07C 233/33* (2013.01); *C07C 235/60* (2013.01); *C07C 235/62* (2013.01); *C07C 237/38* (2013.01); *C07C 237/40* (2013.01); *C07C 237/42* (2013.01); *C07C 237/44* (2013.01); *C07C 251/48* (2013.01); *C07C 275/42* (2013.01); *C07C 311/08* (2013.01); *C07D 209/42* (2013.01); *C07D 213/81* (2013.01); *C07D 215/28* (2013.01); *C07D 223/24* (2013.01); *C07D 223/28* (2013.01); *C07D 231/56* (2013.01); *C07D 235/18* (2013.01); *C07D 235/26* (2013.01); *C07D 249/06* (2013.01); *C07D 261/08* (2013.01); *C07D 263/32*
(2013.01);(Continued)

(58) Field of Classification Search
USPC ................. 514/359, 616; 564/158; 548/360.1
See application file for complete search history.

(56) References Cited

U.S. PATENT DOCUMENTS

| 3,773,919 A | 11/1973 | Boswell et al. | |
|---|---|---|---|
| 6,001,879 A * | 12/1999 | Seitz ..................... | C07C 235/58 514/616 |

(Continued)

FOREIGN PATENT DOCUMENTS

| WO | WO-2009/066258 A1 | 5/2009 |
|---|---|---|
| WO | WO-2010/134039 A2 | 11/2010 |
| WO | WO-2012/070015 A1 | 5/2012 |

OTHER PUBLICATIONS

Dickie, J.P., et al. (1963) "The chemistry of Antimycin A. XI. N-substituted 3-Fomamidosalicylic amides", *Journal of Medicinal Chemistry*, 6(4):424-427.

(Continued)

*Primary Examiner* — Rei-Tsang Shiao
(74) *Attorney, Agent, or Firm* — Harness, Dickey and Pierce, P.L.C.

(57) ABSTRACT

The present invention relates to inhibitors of the activity of Complex (III) of the mitochondrial electron transport chain and use thereof in treatment and/or prevention of cancers presenting tumor-initiating cells. The present invention further relates to pharmaceutical compositions containing said inhibitors alone or in combination with other pharmaceutically active agents, and their use as medicaments or as agrochemicals where their properties as inhibitors of the mitochondrial respiration is of benefit.

13 Claims, 2 Drawing Sheets

(51) Int. Cl.

| | |
|---|---|
| *C07D 213/81* | (2006.01) |
| *C07D 215/28* | (2006.01) |
| *C07C 275/42* | (2006.01) |
| *C07C 39/30* | (2006.01) |
| *C07D 231/56* | (2006.01) |
| *C07C 311/08* | (2006.01) |
| *C07D 235/26* | (2006.01) |
| *C07D 405/12* | (2006.01) |
| *C07C 215/50* | (2006.01) |
| *C07D 249/06* | (2006.01) |
| *C07C 233/25* | (2006.01) |
| *C07D 263/32* | (2006.01) |
| *C07D 263/34* | (2006.01) |
| *C07D 487/10* | (2006.01) |
| *C07C 237/38* | (2006.01) |
| *C07C 237/42* | (2006.01) |
| *C07C 251/48* | (2006.01) |
| *C07D 209/42* | (2006.01) |
| *C07D 305/06* | (2006.01) |
| *C07C 49/825* | (2006.01) |
| *C07D 403/12* | (2006.01) |
| *C07D 223/28* | (2006.01) |
| *C07D 235/18* | (2006.01) |
| *C07C 233/33* | (2006.01) |
| *C07D 261/08* | (2006.01) |
| *C07C 235/60* | (2006.01) |
| *C07C 235/62* | (2006.01) |
| *C07D 263/57* | (2006.01) |
| *C07D 491/107* | (2006.01) |
| *C07C 237/40* | (2006.01) |
| *C07C 237/44* | (2006.01) |
| *C07D 277/56* | (2006.01) |
| *C07D 513/10* | (2006.01) |
| *C07D 305/08* | (2006.01) |
| *A01N 31/08* | (2006.01) |
| *A01N 33/10* | (2006.01) |
| *A01N 35/04* | (2006.01) |
| *A01N 37/24* | (2006.01) |
| *A01N 37/40* | (2006.01) |
| *A01N 37/44* | (2006.01) |
| *A01N 37/46* | (2006.01) |
| *A01N 37/50* | (2006.01) |
| *A01N 43/20* | (2006.01) |
| *A01N 43/38* | (2006.01) |
| *A01N 43/40* | (2006.01) |
| *A01N 43/42* | (2006.01) |
| *A01N 43/46* | (2006.01) |
| *A01N 43/52* | (2006.01) |
| *A01N 43/56* | (2006.01) |
| *A01N 43/60* | (2006.01) |
| *A01N 43/647* | (2006.01) |
| *A01N 43/76* | (2006.01) |
| *A01N 43/78* | (2006.01) |
| *A01N 43/80* | (2006.01) |
| *A01N 43/90* | (2006.01) |
| *A01N 47/30* | (2006.01) |
| *C07C 39/24* | (2006.01) |
| *C07C 43/178* | (2006.01) |
| *C07C 49/245* | (2006.01) |
| *A61K 31/137* | (2006.01) |
| *A61K 31/167* | (2006.01) |
| *A61K 31/17* | (2006.01) |
| *A61K 31/18* | (2006.01) |
| *A61K 31/397* | (2006.01) |
| *A61K 31/421* | (2006.01) |
| *A61K 31/44* | (2006.01) |
| *A61K 31/47* | (2006.01) |
| *A61K 31/55* | (2006.01) |
| *A61K 45/06* | (2006.01) |
| *C07D 223/24* | (2006.01) |

(52) U.S. Cl.
CPC ......... *C07D 263/34* (2013.01); *C07D 263/57* (2013.01); *C07D 277/56* (2013.01); *C07D 305/06* (2013.01); *C07D 305/08* (2013.01); *C07D 403/12* (2013.01); *C07D 405/12* (2013.01); *C07D 487/10* (2013.01); *C07D 491/107* (2013.01); *C07D 513/10* (2013.01); *C07C 2101/04* (2013.01); *C07C2101/14* (2013.01); *C07C 2101/18* (2013.01); *C07C 2102/08* (2013.01); *C07C 2102/42* (2013.01); *C07C 2103/74* (2013.01)

(56) References Cited

U.S. PATENT DOCUMENTS

| | | |
|---|---|---|
| 6,211,376 B1 | 4/2001 | Romines et al. |
| 6,297,401 B1 | 10/2001 | Miesel et al. |
| 6,548,549 B1 * | 4/2003 | Seitz et al. .................. 514/619 |
| 6,713,454 B1 | 3/2004 | Ekwuribe et al. |
| 2005/0171328 A1 | 8/2005 | Harris |
| 2006/0014811 A1 | 1/2006 | Muto et al. |

OTHER PUBLICATIONS

Ford, R.E., et al. (1986) "Synthesis and quantitative structure-activity relationships of antiallergic 2-Hydroxy-*N*-1*H*-tetrazol-5-ylbenzamides and *N*-(2-Hydroxyphenyl)-1*H*-tetrazole-5-carboxamides", *J. Med. Chem.*, 29:538-549.

International Search Report and Written Opinion dated Sep. 10, 2013 issued in PCT Application No. PCT/EP2013/060670.

Macielag, M.J., et al. (1998) "Substituted salicylanilides as inhibitors of two-component regulatory systems in bacteria", *J. Med. Chem.*, 41:2939-2945.

Usuki, Y., et al. (2001) "UK-2A, B, C and D, novel antifungal antibiotics from *Streptomyces* sp. 517-02: VI(1). Structure-activity relationships of UK-2A", *The Journal of Antibiotics*, 54(7):600-602.

* cited by examiner

INHIBITORS OF THE ACTIVITY OF COMPLEX (III) OF THE MITOCHONDRIAL ELECTRON TRANSPORT CHAIN AND USE THEREOF

PRIORITY STATEMENT

This application is a national stage application under 35 U.S.C. §371 of PCT International Application No. PCT/EP2013/060670, which has an international filing date of 23 May 2013 and claims priority under 35 U.S.C. §119 to Switzerland Application No. 00715/12 filed 23 May 2012. The contents of each application recited above are incorporated herein by reference in their entirety.

FIELD OF THE INVENTION

The present invention relates to inhibitors of the activity of Complex (III) of the mitochondrial electron transport chain and use thereof in treatment and/or prevention of cancers presenting tumour-initiating cells. The present invention further relates to pharmaceutical compositions containing said inhibitors alone or in combination with other pharmaceutically active agents, and their use as medicaments or as agrochemicals where their properties as inhibitors of the mitochondrial respiration is of benefit.

BACKGROUND OF THE INVENTION

Cancer affects people at all ages with the risk for most types increasing with age. Cancers are mainly due to genetic deregulations of cells and to lifestyle and environmental factors, which cause abnormalities in the genetic material of cells. For example brain tumours make up to 2% of all tumours in adults and, in their malignant form (grade IV or glioblastoma (GBM)) remain one of the most aggressive diseases with a 2-years survival rate of 32% with today's available standard treatments. It is reported that 1 out of 166 humans are diagnosed with brain tumour once in their lifetime (lifetime risk). Although combining chemotherapy with radiation shows a significant benefit for patients suffering from glioblastoma (GBM), the mean survival rate remains dismal, 16 months on average. Neither genetic factors nor environmental risk factors have been identified and little is known about the biological mechanisms involved in the initiation and progression phases of these brain tumours.

The treatment of cancers is one of the most heavily investigated areas in biomedical research today. Although many anticancer drugs have been and continue to be discovered, there remains the immense problem of developing drugs which will efficiently address this disease and avoid it recurrence.

Many current therapeutic strategies make the assumption that the biology and metabolism of every single cancer cell, including glioma cells, is similar and unfortunately did not provide a significant progress in the treatment of cancers, including glioma.

The recent identification of Stem-like Cells (SC) in a number of human cancers like acute myeloid leukemias (AML), breast, melanoma, colon and brain tumours has renewed interest in the hypothesis that cancers may arise from somatic mutations in adult stem/progenitor cells. A minor population of cancer stem-like cells is likely to represent the source of tumour cell expansion, recurrence and metastasis, thus determining the biological behaviour of tumours including proliferation, progression, and subsequently response to therapy.

Targeting tumour-initiating cells remains challenging due to their rarity, instability in culture and the absence of robust tracer agents. So far, no efficient treatment against tumour-initiating cells has shown a complete eradication of the tumour growth or absence of recurrence in any of the orthotopic xenograft and/or transgenic mouse model. The resistance of tumour-initiating cells to conventional radiotherapy has been demonstrated (Bao et al., 2006; Clement et al., 2007). For example it is known that glioma-initiating cells are resistant to chemotherapeutic agents like temozolomide. These data might explain the inevitable recurrence of gliomas and define tumour-initiating cells as novel targets to overcome the resistance to conventional therapy in this disease.

Because it was shown that tumour-initiating cells (TICs) are actively chemo- and radio-resistant, including brain tumours, there is therefore a need to develop new active agents against the TICs reservoir which may be useful in the treatment of such cancers presenting tumour-initiating cells.

SUMMARY OF THE INVENTION

One object of the present invention is to provide a compound of formula I:

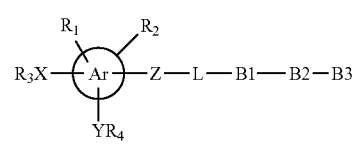

or a pharmaceutically acceptable salt or solvate thereof, wherein:

Ar is selected from $(C_5\text{-}C_{10})$aromatic ring, $(C_5\text{-}C_{10})$heteroaromatic ring where one or more of the carbon atoms in the ring system is replaced by heteroatoms selected from the group consisting of O, S, and N, or $(C_{11}\text{-}C_{12})$-benzofused heteroaromatic cycle where one or more of the carbon atoms in the ring system is replaced by heteroatoms selected from the group consisting of O, S, and N;

$R^1$ and $R^2$ are independently of each other selected from —H, —$(C_1\text{-}C_{10})$alkyl, -aryl, —OH, —O—$(C_1\text{-}C_{10})$alkyl, —O-aryl, —$NH_2$, —NH(CHO), —NH(C=O)—$(C_1\text{-}C_{10})$alkyl, halogen, —$NO_2$, —C(=O)OH, —C(=O)O$(C_1\text{-}C_{10})$alkyl, —$CF_3$, —NH(C=O)($CF_3$(OMe))Ph, $CHF_2$;

X is selected from covalent bond, —H, —O—, —NH—, —$CH_2$—;

Y is selected from covalent bond, —H, —O—, —NH—, —$CH_2$—;

R3 and R4 are independently of each other selected from —H, —$(C_1\text{-}C_{10})$alkyl, -aryl, —C(=O)OH, —C(=O)O($C_1$-$C_{10}$)alkyl, —$CF_3$, —NH(C=O)($CF_3$(OMe))Ph, —$CHF_2$, —C(=O)$CH_2CO_2H$, —$SO_2$($C_1\text{-}C_{10}$)alkyl, —C(=O)$CF_3$, —C(=O)NH($C_1\text{-}C_{10}$)alkyl, or when X and Y are both —NH—, $R_3$ and $R_4$ form together a carbonyl group (C(=O)), with the proviso that if X is —H, than $R_3$ is nothing and if Y is —H, then $R_4$ is nothing;

Z is selected from covalent bond, —NH—, —$CH_2$—; —O—; —C(=O)NH—;

L is selected from: covalent bond, —O—, —S—, —S(O)—, —$S(O)_2$—, —NR—, —C(O)O—, —C(O)NR—, —S(O)NR—, —$S(O)_2$NR—, —CR'R"—, —CR'R"O—, —CR'R"NR—, —C(=NOR)—, —C(=O)—, —(CH=CHOMe)-, —C(CH$_2$OCH$_2$)—, —C(CH$_2$SCH$_2$)—, —C(CH$_2$S(O)$_2$CH$_2$)—, —C(CH$_2$N(R)CH$_2$)—, cyclobut-3-ene-1,2-dione, —C$_6$-aryl, substituted —C$_6$-aryl by —(C$_1$-C$_3$)alkyl, halogens or —CnHmFp where n, m and p are between 1 and 7, —(C$_5$-C$_6$)heteroaryl, substituted —(C$_5$-C$_6$)heteroaryl by —(C$_1$-C$_3$)alkyl, halogens or —CnHmFp where n, m and p are between 1 and 7;

R, R' and R" being independently of each other —H or —(C$_1$-C$_6$)alkyl.

B1 is selected from covalent bond, —O—, —NH, —C(=O)—;

B2 is selected from covalent bond, —(C$_1$-C$_6$)alkyl, —(C$_1$-C$_6$)cycloalkyl, —(C$_1$-C$_{10}$)spirocycloalkyl, where one or several —CH$_2$— unites are replaced by heteroatoms, such as O or S, or by —NMe-, —SO$_2$— or —C(Me)$_2$-;

B3 is selected from covalent bond, —H, optionally substituted —(C$_3$-C$_{30}$)alkyl, optionally substituted —(C$_3$-C$_{30}$)cycloalkyl, optionally substituted —(C$_3$-C$_{30}$)alkylaryl, optionally substituted —(C$_3$-C$_{30}$)cycloalkylaryl, optionally substituted (C$_7$-C$_{30}$)spirocycloalkyl, wherein substituent is one or more heteroatom selected from N, O, S, and/or wherein one or more of carbon atoms is replaced by a heteroatom selected from N, O, S to form ethers (—O—), amines (—NR*—), or amides (—C(O)NR*—) wherein R* is selected from —H, —(C$_1$-C$_6$)alkyl or benzyl.

A further object if the present invention is the compound of formula I according to the invention for use in a method for treating or preventing cancers presenting tumour-initiating cells.

Another object of the present invention is a pharmaceutical composition comprising a therapeutically effective amount of the compound of the invention and a pharmaceutically acceptable carrier.

Another object of the present invention is a kit comprising the compound according to the invention or the pharmaceutical composition of the invention.

Still another object of the present invention is the use of the compound of the invention as antibacterial agent, antifungal agent, pesticide agent and/or herbicide agent.

DETAILED DESCRIPTION OF THE INVENTION

Figure 1:
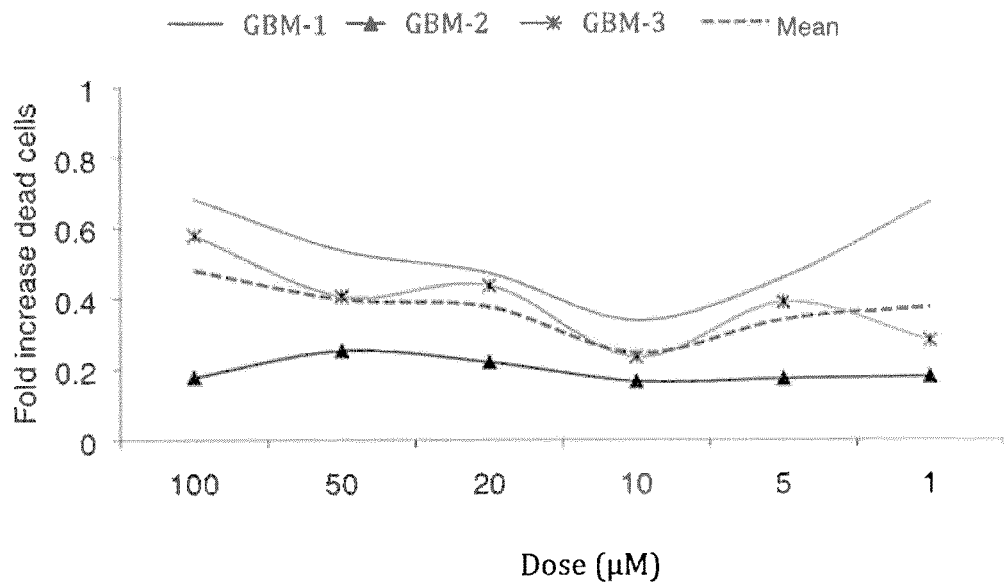
FIG. 1 shows dose response experiment. GICs were exposed to various doses of the compound of Example 19 for 48 hrs. Cell death was measured by incorporating trypan blue and was quantified by Flow cytometry. GBM stands for Glioblastoma Multiforme, -1,-2,-3 represents GBM from various patients

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the term "comprise" is generally used in the sense of include, that is to say permitting the presence of one or more features or components.

As used in the specification and claims, the singular form "a", "an" and "the" include plural references unless the context clearly dictates otherwise.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder, such as cancer, preferably glioma and/or cancers presenting tumour-initiating cells. However, in other embodiments, the subject can be a normal subject or a subject who has already undergone a treatment, such as for example a prior removal of tumour bulk, for example a tumour glioma bulk. The term does not denote a particular age or sex. Thus, adult and newborn subjects, whether male or female, are intended to be covered.

As used herein, the terms "the compound of formula I" or "the compound of the invention" or "the pharmaceutical composition of the invention" also include pharmaceutically acceptable salts or solvates thereof.

The term "alkyl" used alone or in combination with other groups should be understood to include straight chain and branched aliphatic hydrocarbon chain having from 1 to 30, preferably 1 to 6, or 1 to 10, or 3 to 30. Alkyl groups may be optionally substituted with one or more substituents. Non-limiting examples of suitable alkyl groups include methyl, ethyl, n-propyl, i-propyl, n-butyl, i-butyl, t-butyl, n-pentyl, n-hexyl. The optional substituents of alkyl group are independently selected from —H, —(C$_1$-C$_6$)alkyl, —OR', —NR'R", —OC(=O)OR', —C(=O)OR', —C(=O)NR'R", —CF$_3$, —CN, —NO$_2$ or halogen, wherein R, R' and R" represent —H or —(C$_1$-C$_6$)alkyl. The term "branched" should be understood to represent a linear straight chain hydrocarbon group having one or more lower alkyl groups such as methyl, ethyl or propyl, attached to it.

The term "halogen" (or "hal" or "halogens") should be understood to include fluoro, chloro, bromo, iodo, preferably fluoro and chloro, most preferably chloro.

The term "cycloalkyl" unless defined otherwise refers to a saturated monocyclic, bicyclic, tricyclic or spirocyclic ring system having 1 to 30, preferably 3 to 30, more preferably 6 to 30 ring atoms or 1 to 10 ring atoms, or 6 to 20 ring atoms. Preferred cycloalkyl groups include cyclopropyl, cyclobutyl, cyclopentyl, cyclohexyl, norbornyl and the like.

The term "spirocycloalkyl" unless defined otherwise refers to a radical wherein "cycloalkyl" has the meaning as defined above, and is a bicyclic organic compound with two cycloalkyl rings connected through just one atom. The rings can be different or identical.

The term "heterocycloalkyl" unless defined otherwise refers to a cycloalkyl group as defined above, wherein one or more of the atoms in the ring system, preferably 1 to 4 is/are replaced by heteroatoms chosen from the group consisting of O, S, and N. Preferred heterocycloalkyl include oxetane, thioxetane, azetidine, tetrahydrofurane, tetrahydropyrane, pyrrolidine, piperidine, piperazine, oxazines, such as morpholine, thiazines and the like.

The term "aryl" unless defined otherwise should be understood to include a monocyclic or bicyclic, aromatic ring system having 5 to 10, preferably 5, 6 or 10, more preferably 5 or 6 ring atoms. Non-limiting examples of suitable aryl groups include phenyl, (1- or 2-)naphthyl or tetraline groups, most preferably phenyl groups.

The term "alkylaryl", such as for example "$(C_3-C_{30})$ alkylaryl", refers to a radical wherein alkyl and aryl have the meanings as defined above. Illustrative examples of an alkyl-aryl group or radical include benzyl, 2-phenylethyl, 3-phenylpropyl, 4-phenylbutyl, 1-naphthylmethyl.

The term "heteroaryl" unless defined otherwise should be understood to include an aromatic ring system of 5 to 10, preferably 5, 6 or 10, more preferably 5 or 6 ring atoms, in which one or more of the atoms in the ring system is/are atoms other than carbon, for example nitrogen, oxygen or sulfur. Preferably, the aromatic heteroaryl is a 5- or 6-membered aromatic ring having 1 to 3 heteroatoms selected from N, O, S, preferably N and O, and benzo-fused derivatives thereof. Examples of suitable 6-membered heteroaryl groups include pyridine, pyrimidine, pyrazine, pyridazine and the like. Examples of useful 5-membered aromatic heteroaryls include furan, pyrrole, triazole, thiazole, isothiazole, imidazole, pyrazole, oxazole and isoxazole. Useful bicyclic groups are benzo-fused ring systems derived from the aromatic heteroaryls named above, e.g., quinoline, phthalazine, quinazoline, benzofuran, phthaleimide and indole. Most preferred examples are pyridine, pyrimidine, oxazole, thiazole, imidazole, triazole, pyrazole, and phthaleimide.

The cyclic groups aryl, heteroaryl, alkyl, cycloalkyl, heterocycloalkyl, alkylaryl can be substituted with one or more substituents, preferably one, two or three substituents, which may be the same or different, and are independently selected from —H, $(C_1-C_6)$alkyl, —OR", —NR'R'", —OC(=O)R", —C(=O)OR", —C(=O)NR"R'", —CH=CHC(=O)OR", —CF$_3$, —CN, —NO$_2$, halogen, —$(C_1-C_6)$alkyl, —$(C_1-C_6)$cycloalkyl, —$(C_1-C_6)$heterocycloalkyl, wherein R, R' and R" represent —H or $(C_1-C_6)$alkyl.

Applicants have found that tumour-initiating cells (TICs), such as glioma-initiating cells (GICs), (more specifically the FL1$^+$ cell population as used herein) do produce their energy, divide, and survive using the aerobic pathway (TCA cycle/oxidative phosphorylation-electron transport chain). The Applicants have also found that for example the glioma-initiating cells (GICs) have a different metabolism than others glioma cells (cancer cells) from the tumour bulk, which preferentially uses the aerobic glycolysis (Warburg's effect). Indeed the Applicants made an interesting finding that FL1$^+$ cells (CICs) are enriched for NADH, for active mitochondria, and active LD. Furthermore, FL1$^+$ cells have lower levels of lactate compared to FL1$^0$ cells, suggesting that FL1$^+$ cells might preferentially used the aerobic-mitochondria pathway to produce ATP.

The identification of the compounds useful in the treatment of cancers presenting tumour-initiating cells implies the use of a reliable selection method to identify, isolate and characterize the whole cancer-initiating cells (CICs) or tumour-initiating cells (TICs) reservoir and a specific and robust method to test the compounds.

Different developed approaches as recently described in international patent application n° PCT/IB2008/054872 and n° PCT/IB2010/052237, were used to isolate and enrich for a subpopulation of cells showing self-renewing and tumor-initiating properties.

Both methods lie on primary cell cultures derived from human specimen and rely on simple and robust phenotypic characteristics of tumor cells to trace and distinguish viable TICs (referred as FL1$^+$ cells) from the non tumourigenic cells (referred as FL1$^0$ cells) independently of any cell surface marker.

The efficacy of a compound in decreasing and/or eradicating the tumour-initiating cells (e.g. recurrence of the cancer initiating cells) may be assayed by detecting the presence of initiating cells in a cell sample after treatment with the compound according to the present invention, for example by a method as described in PCT/IB2008/054872 and PCT/IB2010/052237, i.e. comprising the following steps:

a) Providing a cancer stem cell sample which was treated by a compound or a method according to the invention;
b) Incubating the treated stem cell sample in a stem cell culture medium for an incubation period without treatment;
c) Selecting the viable cell population from the stem cell sample incubated under step (b);
d) Measuring the mean level of autofluorescence on the viable cell population isolated under step (c) by detecting, by fluorescence activated cell sorting, cells presenting autofluorescence emission in the FL1 channel upon laser beam excitation at a wavelength of or about 488 nm;
e) Isolating cells by fluorescence activated cell sorting cell which have a specific morphology (high FSC and low/middle SSC) and present autofluorescence emission in the FL1 channel upon laser beam excitation at a wavelength of or about 488 nm of the viable cell population isolated under step (c);
f) Isolating cells by fluorescence activated cell sorting which have a specific morphology (low/middle FSC and middle/high SSC), do not present autofluorescence emission in the FL1 channel under step (c) and present a slight positive shift in the cell fluorescence emission in the FL3 and/or FL4 channel upon laser beam excitation of the viable cell population isolated under under step (c);
g) Calculating the percentage of autofluorescent viable cells by comparing the mean level of autofluorescence in the cancer stem cell sample provided under step (a) and the mean level of autofluorescence measured under step (d);
h) Calculating the percentage of the cell death by comparing the number of initial cells present in the cancer stem cell sample provided under step (a) and the resulting viable cell population isolated under step (c);
i) Calculating the percentage of viable FL1$^+$ cells by comparing the number of initial FL1$^+$ cells present in the cancer stem cell sample provided under step (a) and the resulting viable FL1$^+$ cell population isolated under step (e);
j) Calculating the percentage of viable FL1$^0$ cells by comparing the number of initial FL1$^0$ cells present in the cancer stem cell sample provided under step (a) and the resulting viable FL1$^0$ cell population isolated under step (f);
k) Detecting spherogenicity of the cell populations detected under steps (e) and (f).

l) Determining the activity of the agent through its ability to inhibit cancer stem cells recurrence.

The in vitro and in vivo phenotypic and behaviour differences between FL1⁺ and FL1⁰ tumour cell populations was supported by further characterization demonstrating that FL1⁺ cells are enriched for sternness-related genes, are multipotent, can generate FL1⁰ cells and are responsible for maintaining the long-term self-renewal capacity overtime. Because FL1⁰ derived cultures do not yield any FL1⁺ cell, it provides further evidence that FL1⁰ cells are derived from the FL1⁺ population, remain viable for several passages, but are unable to reacquire autofluorescent properties once they have switched from the FL1⁺ toward the FL1⁰ state.

Applicants found that compounds, which target the oxidative cellular energy production process, demonstrate a reliable and long-lasting efficacy to eradicate tumour-initiating cells. Compounds which prevents NADH from being converted into cellular ATP at the mitochondrial III and induces the formation of H$_2$O$_2$ generation might therefore be considered as novel and specific therapeutic strategy against tumour-initiating cells.

Applicants also demonstrate that blocking the production of energy generated by the aerobic pathway is sufficient for killing the whole tumour-initiating cell population (the killing is done by starving tumour-initiating cells, and not by apoptosis). Compounds, which can be inhibitors, interfering with the electron transport chain such as the one of mitochondria at the level of the complex III are demonstrating an exceptional capacity to kill every tumour-initiating cells in vitro and in vivo. As the inhibition of complex III results in large production of reactive oxygen species (ROS) and free radicals, it is likely that the tumour-initiating cells are also killed by the accumulation of ROS or the saturation of the detoxification system.

Applicants surprisingly found that the compounds of the present invention are inhibitors of the activity of Complex (III) of the mitochondrial electron transport chain. This finding provides the application of the compounds of the present invention not only in treatment and prevention of cancers presenting tumour-initiating cells, but also in many other fields where the inhibition of the activity of Complex (III) of the mitochondrial electron transport chain is beneficial. This includes, for example, antibacterial, antifungal, pesticide and herbicide applications.

The present invention provides a compound of formula I

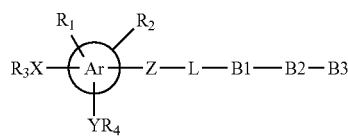

or a pharmaceutically acceptable salt or solvate thereof, wherein:

Ar is selected from (C$_5$-C$_{10}$)aromatic ring, (C$_5$-C$_{10}$)heteroaromatic ring where one or more of the carbon atoms in the ring system is replaced by heteroatoms selected from the group consisting of O, S, and N, or (C$_{11}$-C$_{12}$)-benzofused heteroaromatic cycle where one or more of the carbon atoms in the ring system is replaced by heteroatoms selected from the group consisting of O, S, and N;

R$^1$ and R$^2$ are independently of each other selected from —H, —(C$_1$-C$_{10}$)alkyl, -aryl, —OH, —O—(C$_1$-C$_{10}$)alkyl, —O-aryl, —NH$_2$, —NH(CHO), —NH(C═O)—(C$_1$-C$_{10}$) alkyl, halogen, —NO$_2$, —C(═O)OH, —C(═O)O(C$_1$-C$_{10}$) alkyl, —CF$_3$, —NH(C═O)(CF$_3$(OMe))Ph, CHF$_2$;

X is selected from covalent bond, —H, —O—, —NH—, —CH$_2$—;

Y is selected from covalent bond, —H, —O—, —NH—, —CH$_2$—;

R3 and R4 are independently of each other selected from —H, —(C$_1$-C$_{10}$)alkyl, -aryl, —C(═O)OH, —C(═O)O(C$_1$-C$_{10}$)alkyl, —CF$_3$, —NH(C═O)(CF$_3$(OMe))Ph, —CHF$_2$, —C(═O)CH$_2$CO$_2$H, —SO$_2$(C$_1$-C$_{10}$)alkyl, —C(═O)CF$_3$, —C(═O)NH(C$_1$-C$_{10}$)alkyl, or when X and Y are both —NH—, R$_3$ and R$_4$ form together a carbonyl group (C(═O)), with the proviso that if X is —H, than R$_3$ is nothing and if Y is —H, then R$_4$ is nothing;

Z is selected from covalent bond, —NH—, —CH$_2$—; —O—; —C(═O)NH—;

L is selected from: covalent bond, —O—, —S—, —S(O)—, —S(O)$_2$—, —NR—, —C(O)O—, —C(O)NR—, —S(O)NR—, —S(O)$_2$NR—, —CR'R"—, —CR'R"O—, —CR'R"NR—, —C(═NOR)—, —C(═O)—, —(CH═CHOMe)-, —C(CH$_2$OCH$_2$)—, —C(CH$_2$SCH$_2$)—, —C(CH$_2$S(O)$_2$CH$_2$)—, —C(CH$_2$N(R)CH$_2$)—, cyclobut-3-ene-1,2-dione, —C$_6$-aryl, substituted —C$_6$-aryl by —(C$_1$-C$_3$)alkyl, halogens or —CnHmFp where n, m and p are between 1 and 7, —(C$_5$-C$_6$)heteroaryl, substituted —(C$_5$-C$_6$)heteroaryl by —(C$_1$-C$_3$)alkyl, halogens or —CnHmFp where n, m and p are between 1 and 7;

R, R' and R" being independently of each other —H or —(C$_1$-C$_6$)alkyl.

B1 is selected from covalent bond, —O—, —NH, —C(═O)—;

B2 is selected from covalent bond, —(C$_1$-C$_6$)alkyl, —(C$_1$-C$_6$)cycloalkyl, —(C$_1$-C$_{10}$)spirocycloalkyl, where one or several —CH$_2$— unites are replaced by heteroatoms, such as O or S, or by —NMe-, —SO$_2$— or —C(Me)$_2$-;

B3 is selected from covalent bond, —H, optionally substituted —(C$_3$-C$_{30}$)alkyl, optionally substituted —(C$_3$-C$_{30}$)cycloalkyl, optionally substituted —(C$_3$-C$_{30}$)alkylaryl, optionally substituted —(C$_3$-C$_{30}$)cycloalkylaryl, optionally substituted (C$_7$-C$_{30}$)spirocycloalkyl, wherein substituents are one or more heteroatoms selected from N, O, S, and/or wherein one or more of carbon atoms is replaced by a heteroatom selected from N, O, S to form ethers (—O—), amines (—NR*—), or amides (—C(O)NR*—), wherein R* is selected from —H, —(C$_1$-C$_6$)alkyl or benzyl.

Preferably, Ar is C$_6$-aromatic ring.

Preferably Ar is (C$_{11}$-C$_{12}$)-benzofused heteroaromatic cycle where one or more of the carbon atoms in the ring system is replaced by heteroatoms selected from the group consisting of O, S, and N.

Preferably L is selected from —C(O)NH—, —NH—CH$_2$—, oxazole-C(O)NH—, oxazole-NH—, oxazole, pyridines, pyrimidines, pyroles, furanes, thiophenes, imidazoles, pyrzoles, oxazoles, isoxazoles thioxazoles, oxadiazoles, (1,2,3)- and (1,2,4)-triazoles.

Preferably R$^1$ and R$^2$ are H.

Preferably B3 is selected from the group comprising adamantyl, bicyclo[2.2.2]octane, bicyclo[1.1.1]pentanes, quinuclidine, 10,11-dihydro-5H-dibenzo[b,f]azepine, optionally substituted with (C$_1$-C$_3$)alkyls, halogens, CF$_3$ groups.

Preferably the compound of formula I is selected from the group comprising:
3-formamido-N-(heptadecan-9-yl)-2-hydroxybenzamide;
N-cyclopentadecyl-7-hydroxy-1H-indazole-6-carboxamide;
3,5-dichloro-N-(3-(3-chloro-10,11-dihydro-5H-dibenzo[b,f] azepin-5-yl)-2-hydroxybenzamide;

2-(3-formamido-2-hydroxybenzamido)-2,3-dihydro-1H-inden-1-yl octanoate;
N-cyclopentadecyl-3-formamido-2-hydroxybenzamide;
N-cyclododecyl-3-formamido-2-hydroxybenzamide
3,5-dichloro-N-cyclopentadecyl-2-hydroxybenzamide
3,5-dichloro-N-decyl-2-hydroxybenzamide
N-(3,5-dichloro-2-hydroxyphenyl)undecanamide
N-(4-(cyclopentadecylcarbamoyl)phenyl)-3-formamido-2-hydroxybenzamide
N-(heptadecan-9-yl)-2-oxo-2,3-dihydro-1H-benzo[d]imidazole-4-carboxamide
N-(3-(3-chloro-10,11-dihydro-5H-dibenzo[b,f]azepin-5-yn) propyl)-7-hydroxy-1H-imidazole-6-carboxamide
N-(3-(3-chloro-10,11-dihydro-5H-dibenzo[b,f]azepin-5-yl) propyl)-3-formamido-2-hydroxybenzamide
N-(3-(10,11-dihydro-5H-dibenzo[b,f]azepin-5-yl)propyl)-3-formamido-2-hydroxybenzamide
N-(3-(1-(heptadecan-9-yl)-1H-1,2,3-triazol-4-yl)-2-hydroxyphenyl)formamide
N-(3-(1-cyclopentadecyl-1H-1,2,3-triazol-4-yl)-2-hydroxyphenyl)formamide
N-cyclononyl-7-hydroxy-1H-indazole-6-carboxamide
N-cyclononyl-2-oxo-2,3-dihydro-1H-benzo[d]imidazole-4-carboxamide
N-cyclopentadecyl-2-oxo-2,3-dihydro-1H-benzo[d]imidazole-4-carboxamide More preferably the compound of formula I is selected from the group comprising:
3-formamido-N-(heptadecan-9-yl)-2-hydroxybenzamide;
N-cyclopentadecyl-7-hydroxy-1H-indazole-6-carboxamide;
3,5-dichloro-N-(3-(3-chloro-10,11-dihydro-5H-dibenzo[b,f]azepin-5-yl)-2-hydroxybenzamide It is further understood that all isomers, including enantiomers, stereoisomers, rotamers, tautomers and racemates of the compound(s) of formula I are contemplated as being part of this invention. The invention includes stereoisomers in optically pure form and in admixture, including racemic mixtures. Isomers can be prepared using conventional techniques, either by reacting optically pure or optically enriched starting materials or by separating isomers of a compound of formula I.

A skilled person will know that, if a compound of the invention contains charged group, a suitable counterion will be derived from an organic or inorganic acid. Such counterions include halide (such as chloride, bromide, fluoride, iodide), sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. If the polar moiety is a negatively charged group, a suitable counterion will be selected from sodium, ammonium, barium, calcium, copper, iron, lithium, potassium and zinc, and the like.

According to the present invention, pharmaceutically acceptable salts are produced from acidic inorganic or organic compounds, or alkaline inorganic or organic compounds.

As used herein, the phrase "pharmaceutically acceptable salt" refers to a salt that retains the biological effectiveness of the free acids and bases of a specified compound and that is not biologically or otherwise undesirable. The pharmaceutically acceptable salts of the compounds of formula (I) are acid addition salts with pharmaceutically acceptable acids.

A desired salt may be prepared by any suitable method known in the art, including treatment of the free base with an inorganic acid, such as hydrochloric acid, hydrobromic acid, sulphuric acid, nitric acid, phosphoric acid, and the like, or with an organic acid, such as formic acid, acetic acid, maleic acid, succinic acid, mandelic acid, maleic acid, fumaric acid, malonic acid, pyruvic acid, oxalic acid, glycolic acid, salicylic acid; a pyranosidyl acid, such as glucuronic acid or galacturonic acid; an alpha-hydroxy acid, such as citric acid or tartaric acid; an amino acid, such as aspartic acid or glutamic acid; an aromatic acid, such as benzoic acid or cinnamic acid; a sulfonic acid, such as methanesulfonic acid, p-toluenesulfonic acid or ethanesulfonic acid; or the like.

In the present invention the preferred ammonium salts are derived from hydrochloric, hydrobromic, methanesulfonic, acetic, propionic, benzoic, citric, tartaric, malic, maleic, fumaric, lactic, nitric, and phosphoric or succinic acid.

Generally, the salts are prepared by reacting the free base with stoichiometric amounts or with an excess of the desired salt forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, symmetrical or asymmetrical ethers containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt from the mixture, or it can be precipitated by the addition of a solvent in which the salt is insoluble and recovered there from.

Examples of suitable inorganic and organic solvents for performing the various reactions include any inorganic or organic solvent that does not adversely affect the reactants or the resulting product, including halogenated solvents such as methylene chloride, chloroform, ether solvents such as diethyl ether, and other solvents such as tetrahydrofuran, dioxane, diglyme, cyclooctane, benzene or toluene, heptane, cyclohexane, aliphatic as well as cycloaliphatic and aromatic hydrocarbon solvents, water, acidified aqueous solutions, mixed organic and inorganic solutions, ethyl acetate, propyl acetate and mixtures thereof.

Also encompassed by the present invention are salts formed from acidic prodrugs, such as phosphates, and alkaline inorganic or organic compounds. Preferred inorganic cations comprised in the salts are lithium, sodium, potassium, rubidium, ammonium, calcium, magnesium, zinc and manganese. Production of phosphate salts are described in e.g. G. R. Pettit et al. *Anti-Cancer Drug Design* 16 (2001) 185-193.

Preferred salts also include those formed from acidic prodrugs and organic amines, including, but not limited to, imidazole and morpholine. Alkaline amino acid salts may also be used. The term "amino acids" designates, according to the invention, in particular the [alpha]-amino acids occurring in nature, but moreover also includes their homologues, isomers and derivatives. Enantiomers can be mentioned as an example of isomers. Derivatives can be, for example, amino acids provided with protective groups. Preferred alkaline amino acid are arginine, ornithine, diaminobutyric acid, lysine or hydroxy lysine and especially L-arginine, L-lysine or L-hydroxy lysine; an alkaline dipeptide or a pharmaceutically acceptable alkaline amino acid derivate.

A "pharmaceutically acceptable solvate" or "solvate" refers to an aggregate or physical association of a compound of the present invention with one or more solvent molecules. The solvent may be water or any common organic solvent.

This physical association involves varying degrees of ionic and covalent bonding, including hydrogen bonding. In certain embodiments, the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are H20.

The present invention also relates to pro-drugs of a compound of formula I that in vivo convert to the compound of formula I as such. Any reference to a compound of formula I is therefore to be understood as referring also to the corresponding pro-drug of the compound of formula I, as appropriate.

For the purposes of the present invention, a "pro-drug" is an entity which either comprises an inactive form of an active drug (parent compound) or includes a chemical group which confers preferred characteristics on the drug. In other words, it concerns a composition which has the potential of producing a desired physiological effect on cells, but is initially inert (i.e. does not produce said effect), and only after undergoing some modifications becomes physiologically active and produces said physiological effect on cells. In particular, the derivative of the compound of formula I has a chemically or metabolically degradable group, and becomes pharmaceutically active after biotransformation.

Biotransformation of the prodrug or a salt thereof is carried out under physiological conditions (in vivo) and is a result of a reaction with an enzyme, or a body fluid such as gastric acid, blood etc., thus undergoing an enzymatic oxidation, reduction, hydrolysis etc. or a chemical hydrolysis convert into the active parent compound of formula I.

As used herein, the terms "parent compounds" or "active parent compounds" or "active drugs" are used interchangeably herein to designate the compounds of formula I according to the present invention.

The term "physiological effect" concerns any effect a drug may have on cells, in order to improve the health of the subject administered with the drug. The effect is produced in order to treat, prevent a disease, a defect or pathological condition or to alleviate some of the manifestations of a disease, defect or pathological condition.

The invention also encompasses chemical modifications of the compounds of formula I to prolong their circulating lifetimes. Examples of suitable poly(ethylene glycol) derivatives that possess this property are described in e.g. US 2005171328 (NEKTAR THERAPEUTICS AL CORP) or U.S. Pat. No. 6,713,454 (NOBEX CORP). Since the compounds of formula I are fairly lipophilic, the PEG-oligomer/polymer also increases the hydrophilicity of the pro-drugs and thereby their aqueous solubility.

The selection method and the process method of an appropriate prodrug derivative are described in the literature such as *Design of Prodrugs*, Elsevier, Amsterdam 1985; G. R. Pettit et al. *Anti-Cancer Drug Design* 16 (2001) 185-193.

The compound(s) of formula (I) according to the present invention, their pharmaceutically acceptable salts and pro-drugs thereof, where applicable, may be administered in the form of a pharmaceutical composition in which they are in association with a pharmaceutically acceptable adjuvant, diluent or carrier, in order to prevent or treat any disease in which the compounds of the present invention would be considered beneficial by the skilled person.

The present invention also provides a pharmaceutical composition comprising a compound of formula (I), or a pharmaceutically acceptable salt thereof, as hereinbefore defined, in association with a pharmaceutically acceptable adjuvant, diluent or carrier. As to the appropriate excipients, diluents and adjuvants, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik and angrenzende Gebiete", by H. P. Fiedler, Editio Cantor, 2002.

The compound(s) of formula (I) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, *Osol, A. Ed.* (1980).

Sustained-release preparations may be prepared. Suitable examples of sustained-release preparations include semi permeable matrices of solid hydrophobic polymers containing the compounds of formula (I), which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The pharmaceutical compositions of the invention may be also formulated as creams, gels, solutions, ointments, suspensions or plasters etc. when intended for topical administration; for administration by inhalation, e.g. as aerosols or dry powders; for oral administration, e.g. in the form of tablets, capsules, gels, syrups, suspensions, solutions, powders or granules; for rectal or vaginal administration e.g. as suppositories; or for parenteral injection (including intravenous, subcutaneous, intramuscular, intravascular, or infusion) as a sterile solution, suspension or emulsion.

Applicants have found that the compounds of the present invention are inhibitors of the activity of Complex (III) of the mitochondrial electron transport chain are useful in methods of treatment and/or prevention of a subject, preferably a mammalian subject, who is suffering from cancers presenting tumour-initiating cells (GICs). Preferably cancers presenting tumour-initiating cells are selected from the group comprising human gliomas, schwanommas, metastasis to the brain, meningiomas, ependymomas, a metastatic cancer such as for example melanoma, breast cancer, colon cancer or lung cancer.

The present invention further provides a compound of formula I as per present invention or a pharmaceutically acceptable salt or solvate thereof, for use in a method for treatment or prevention of cancers presenting tumour-initiating cells.

Preferably said cancers presenting tumour-initiating cells are selected from the group comprising human gliomas, schwanommas, metastasis to the brain, meningiomas, ependymomas, a metastatic cancer such as melanoma, breast cancer, colon cancer or lung cancer. More preferably the cancers presenting tumour-initiating cells is a cancer involving GICs.

In a particular embodiment, the present invention provides a method for treating or preventing cancers presenting tumour-initiating cells comprising administering to a subject in need of such treatment a therapeutically effective amount of the compound of the invention or the pharmaceutical composition of the invention.

The daily dose of compounds of the present invention will necessarily be varied depending upon the host treated, the particular route of administration, and the severity and kind of the illness being treated. Accordingly the optimum dosage may be determined by the practitioner who is treating any particular patient.

The present invention further provides a pharmaceutical composition comprising a therapeutically effective amount of the compound of the present invention and pharmaceutically acceptable carrier. Optionally, the pharmaceutical composition of the present invention further comprises one or more additional active agents.

"Treatment" refers to both therapeutic treatment and prophylactic or preventative measures. Those in need of treatment include those already with the disorder, for example cancer, preferably glioma and/or cancers presenting tumour-initiating cells, as well as those in which the disorder, for example cancer, is to be prevented. Hence, the mammal to be treated herein may have been diagnosed as having the disorder, for example cancer, or may be predisposed or susceptible to the disorder, for example cancer, preferably glioma and/or cancers presenting tumour-initiating cells.

"Mammal" for purposes of treatment refers to any animal classified as a mammal, including humans, domestic and farm animals or pet animals, such as dogs, horses, cats, cows, monkeys etc. Preferably, the mammal is human.

The term "therapeutically effective amount" refers to an amount of a drug effective to treat a disease or disorder in a mammal. In the case of cancer, the therapeutically effective amount of the a compound of the present invention may reduce the number of cancer cells, more specifically tumour-initiating cell (TICs) and/or glioma-initiating cells (GICs); reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; and/or relieve to some extent one or more of the symptoms associated with the cancer. To the extent the compound of the present invention may prevent growth and/or kill existing cancer cells, more specifically tumour-initiating cell (TICs) and/or glioma-initiating cells (GICs), it may be cytostatic and/or cytotoxic. The phrase "therapeutically effective amount" is used herein to mean an amount sufficient to prevent, or preferably statistically reduce a clinically significant change in the growth or progression or mitotic activity of a target cellular mass, group of cancer cells or tumour, or other feature of pathology.

The terms "cancer" and "cancerous" refer to or describe the physiological condition in mammals that is typically characterized by unregulated cell growth. According to the present invention, cancer refers preferably to cancers presenting tumour-initiating cells (TICs), in particular human gliomas (GICs), schwanommas, metastasis to the brain, meningiomas, ependymomas, a metastatic cancer such as for example melanoma, breast cancer, colon cancer or lung cancer.

Optionally the compounds of formula (I) according to the present invention may be used against cell proliferate diseases in combination with conventional treatments such as standard radiotherapy and/or standard chemotherapy. The standard radiotherapy and chemotherapy can be also the concomitant chemo-radiotherapy.

The term "concomitant chemo-radiotherapy" is used when these two treatments (chemotherapy and radiotherapy) are given either at the same time, or almost at the same time, for instance one after the other, or on the same day, etc.

The term "standard radiotherapy" refers to the use of ionizing radiation as part of cancer treatment to control malignant cells. Preferably the ionizing radiation is γ-irradiation. It is also common to combine radiotherapy with surgery, chemotherapy, hormone therapy, or combinations thereof. Most common cancer types can be usually treated with radiotherapy. The precise treatment intent (curative, adjuvant, neoadjuvant or palliative) will depend on the tumour type, location, and stage, as well as the general health of the subject in need thereof.

The term "standard chemotherapy" generally refers to a treatment of a cancer using specific chemotherapeutic/chemical agents. A chemotherapeutic agent refers to a pharmaceutical agent generally used for treating cancer. The chemotherapeutic agents for treating cancer include, for example, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide, Tioguanine/Thioguanine, Thiotepa, Topotecan, Treosulfan, Vinblastine, Vincristine, Vindesine or Vinorelbine.

When a chemotherapeutic agent selected from the agents listed-above, or at least one chemotherapeutic agent selected from the agents listed-above, is used in combination with the compounds of formula (I) according to the present invention, then this may be used in the form of a medicament containing a combination of these two agents, for simultaneous administration, or they may be used in the form of separate dosage forms, each containing one of the agents, and in the latter case the individual dosage forms may be used e.g. sequentially, i.e. one dosage form with the compound (I), followed by a dosage form containing the chemotherapeutic agent (or vice versa). This embodiment of two separate dosage forms may be conceived and provided in the form of a kit.

Generally, the kit comprises a container and a label or package insert on or associated with the container. Suitable containers include, for example, bottles, vials, syringes, etc. The containers may be formed from a variety of materials such as glass or plastic. The container holds the compound's composition or the pro-drug composition or pharmaceutically acceptable salts thereof that are effective for treating the condition and may have a sterile access port (for example the container may be an intravenous solution bag or a vial having a stopper pierceable by a hypodermic injection needle). The label or package insert indicates that the composition is used for treating the condition of choice, such as cancer.

Thus an object of the present invention is also a kit comprising the compound of the present invention or the pharmaceutical composition of the present invention. The kit can further contain one or more chemotherapeutic agent selected from the group comprising Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide Tioguanine/Thioguanine, Thiotepa, Topotecan, Treosulfan, Vinblastine, Vincristine, Vindesine or Vinorelbine.

Since the compounds of the present invention are inhibitors of the activity of Complex (III) of the mitochondrial electron transport chain, the present invention further provides the use of the compound of the invention for many other applications where the inhibition of the activity of Complex (III) of the mitochondrial electron transport chain is beneficial. This includes, for example, antibacterial, antifungal, pesticide and herbicide applications. Therefore the compounds of the present invention can be used in agriculture, in fish farming and in food industry in general. In particular, the present invention provides for the use of the compound of formula I as antibacterial agent, antifungal agent, pesticide agent and/or herbicide agent.

Another useful application of the compound(s) of the present invention is its use as cardiovascular drugs.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Synthesis of Compounds

Typically the compounds of the present invention can be synthesised by adapting the protocols reported by Hu et al. in *Tetrahedron Lett.* 2008, 49, 5192, or Wu et al. in *J. Org. Chem.* 2006, 71, 4296 or Chakraborty et al. in *Tetrahedron Lett.* 2007, 48, 1265. Other heteroatom containing rings (bis-lactam, bis-thiolactones etc.) can be accessed using the same synthetic approach. The cycloalkyl and heterocyloalkyl rings formed by for example by $R^5$ and $R^7$ can be introduced before the closure of the 9-membered ring using methods known by the person skilled in the art, or after closure of the ring, using for example ring-closing methatesis reactions followed by hydrogenation. Metathesis can also be used for the cyclisation of the 9-membered central ring. Examples of ring-closing methasis to synthesize 9-membered ring can be found in Clark et al., *Org. Lett.* 2003, 5, 89.

For examples where the central core is an all-carbon bicycle or a heteroatom containing bicycle, a person skilled in the art will synthesize the corresponding central motif using reactions such as Diels-Alder reaction, before decorating the scaffold with the desired side-chains.

Alternatively, the amino group attached to the ring can be introduced by reductive amination of the corresponding preformed cyclic ketone.

Example 1

3-formamido-2-hydroxy-N-(1,7,7-trimethylbicyclo[2.2.1]heptan-2-yl)benzamide

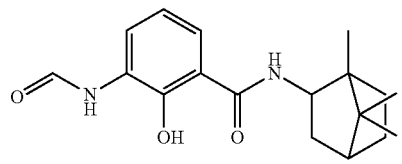 [SMILES: CC1(C)C2CCC1(C)C(NC(=O)c1cccc(NC=O)c1O)C2]

Example 2

2-(3-formamido-2-hydroxybenzamido)-2,3-dihydro-1H-inden-1-yl octanoate

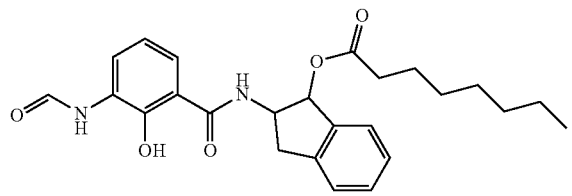 [SMILES: CCCCCCCC(=O)OC1c2ccccc2CC1NC(=O)c1cccc(NC=O)c1O]

Example 3

3-formamido-2-hydroxy-N-(1-hydroxy-2,3-dihydro-1H-inden-2-yl)benzamide

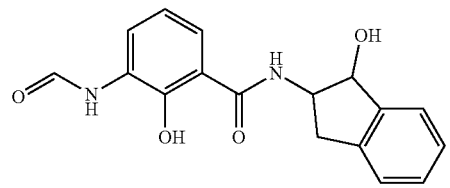 [SMILES: O=CNc1cccc(C(=O)NC2Cc3ccccc3C2O)c1O]

Example 4

N-cyclopentadecyl-3-formamido-2-hydroxybenzamide

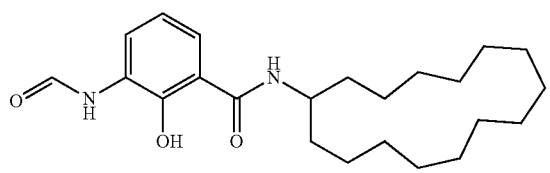 [SMILES: O=CNc1cccc(C(=O)NC2CCCCCCCCCCCCCC2)c1O]

¹H NMR (300 MHz, CDCl₃) δ 13.35 (s, 1H), 8.49 (s, 1H), 8.48 (dd, J=5.8, 1.6 Hz, 1H), 7.98 (s, 1H), 7.11 (d, J=7.9 Hz, 1H), 6.83 (t, J=8.1 Hz, 1H), 6.22 (d, J=8.4 Hz, 1H), 4.22-4.11 (m, 1H), 1.73-1.27 (m, 28H).
LC-MS (ESI): [M+H]⁺=389.2

Example 5

N-adamantan-1-yl-3-formamido-2-hydroxybenzamide

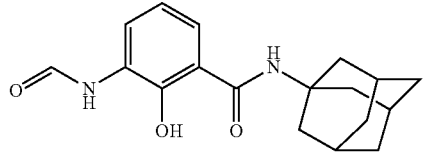 [SMILES: O=CNc1cccc(C(=O)NC23CC4CC(CC(C4)C2)C3)c1O]

Example 6

N-cyclododecyl-3-formamido-2-hydroxybenzamide

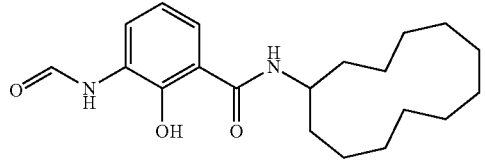 [SMILES: O=CNc1cccc(C(=O)NC2CCCCCCCCCCC2)c1O]

Example 7

N-adamantan-2-yl-3-formamido-2-hydroxybenzamide

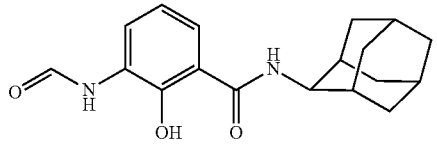 [SMILES: O=CNc1cccc(C(=O)NC2C3CC4CC(C3)CC2C4)c1O]

Example 8

3-formamido-2-hydroxy-N-(4-phenylcyclohexyl)benzamide

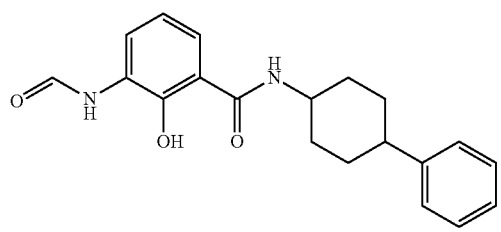 [SMILES: O=CNc1cccc(C(=O)NC2CCC(c3ccccc3)CC2)c1O]

Example 9

3-formamido-2-hydroxy-N-(3,3,5,5-tetramethylcyclohexyl)benzamide

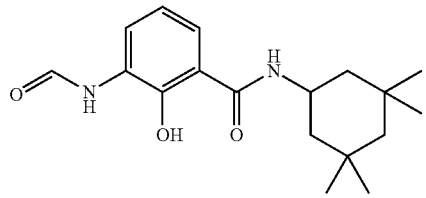 [SMILES: CC1(C)CC(NC(=O)c2cccc(NC=O)c2O)CC(C)(C)C1]

Example 10

N-(4-(tert-butyl)cyclohexyl)-3-formamido-2-hydroxybenzamide

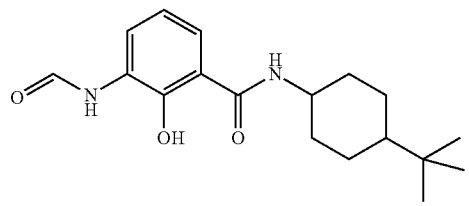 [SMILES: CC(C)(C)C1CCC(NC(=O)c2cccc(NC=O)c2O)CC1]

Example 11

(E)-N-(3,7-dimethylocta-2,6-dien-1-yl)-3-hydroxy-4-methoxypicolinamide

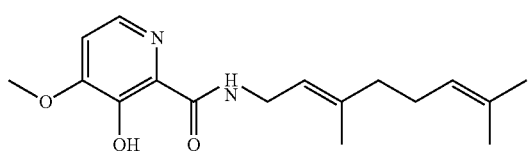 [SMILES: COc1ccnc(C(=O)NC/C=C(\C)CCC=C(C)C)c1O]

¹H NMR (300 MHz, CDCl₃) δ 12.49 (s, 1H), 7.91 (d, J=5.2 Hz, 1H), 6.83 (d, J=5.2 Hz, 1H), 5.26 (t, J=7.1 Hz, 1H), 5.05 (t, J=6.9 Hz, 1H), 4.01 (t, J=6.4 Hz, 2H), 3.99 (br s, 1H), 3.91 (s, 3H), 2.15-1.90 (m, 4H), 1.70 (s, 3H), 1.65 (s, 3H), 1.58 (s, 3H).
LC-MS (ESI): [M+H]⁺=305.1

Example 12

5-chloro-7-((diethylamino)methyl)quinolin-8-ol

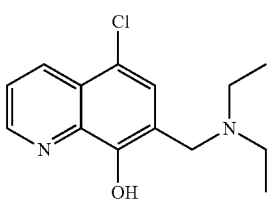 [SMILES: CCN(CC)Cc1cc(Cl)c2cccnc2c1O]

¹H NMR (300 MHz, CDCl₃) δ 10.50 (br s, 1H), 8.91 (dt, J=4.2, 1.1 Hz, 1H), 8.44 (dt, J=8.7, 1.2 Hz, 1H), 7.45 (dd, J=8.5, 4.1 Hz, 1H), 3.91 (s, 2H), 2.69 (q, J=7.2 Hz, 4H), 1.15 (t, J=7.1 Hz, 6H).

Example 13

3,5-dichloro-N-cyclopentadecyl-2-hydroxybenzamide

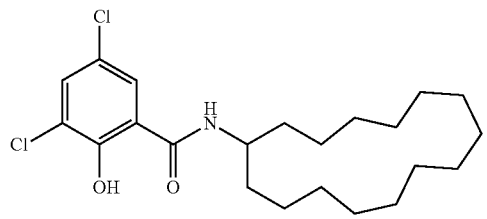 [SMILES: O=C(NC1CCCCCCCCCCCCCC1)c1cc(Cl)cc(Cl)c1O]

¹H NMR (300 MHz, CDCl₃) δ 13.01 (s, 1H), 7.49 (dd, J=2.4, 1.0 Hz, 1H), 7.21 (dd, J=2.4, 1.0 Hz, 1H), 6.18 (d, J=8.2 Hz, 1H), 4.30-4.10 (m, 1H), 2.02-1.42 (m, 28H).
LC-MS (ESI): [M+H]⁺=414.2

Example 14

3,5-dichloro-N-decyl-2-hydroxybenzamide

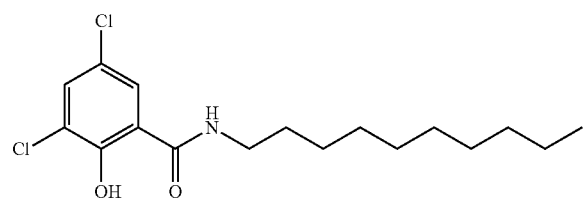 [SMILES: CCCCCCCCCCNC(=O)c1cc(Cl)cc(Cl)c1O]

¹H NMR (300 MHz, CDCl₃) δ 12.96 (s, 1H), 7.48 (d, J=2.3 Hz, 1H), 7.25 (d, J=2.8 Hz, 1H), 6.27 (s, 1H), 3.44 (q, J=6.8 Hz, 2H), 1.68-1.52 (m, 2H), 1.41-1.22 (m, 18H).
LC-MS (ESI): [M+H]⁺=346.1

Example 15

N-cyclononyl-2-hydroxy-3-(methylsulfonamido)benzamide

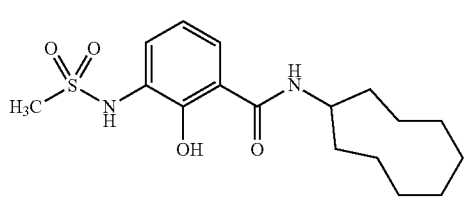 [SMILES: CS(=O)(=O)Nc1cccc(C(=O)NC2CCCCCCCC2)c1O]

¹H NMR (300 MHz, CDCl₃) δ 13.59 (s, 1H), 7.61 (dt, J=7.6, 2.0 Hz, 1H), 7.50 (dd, J=8.0, 1.8 Hz, 1H), 7.37 (t, J=7.9 Hz, 1H), 6.11 (d, J=8.0 Hz, 1H), 4.25-4.10 (m, 1H), 3.38 (d, J=0.9 Hz, 3H), 1.85-1.50 (m, 16H).
LC-MS (ESI): [M+H]⁺=355.2

Example 16

N-cyclononyl-2-hydroxy-3-(3-methylureido)benzamide

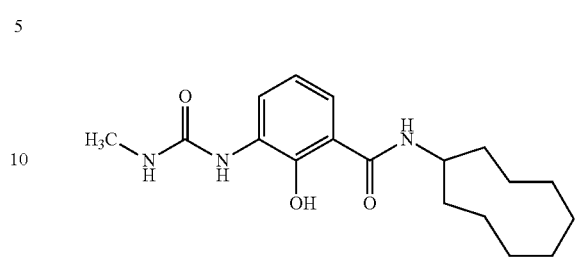

¹H NMR (300 MHz, CDCl₃) δ 13.07 (s, 1H), 8.15 (dd, J=8.0, 1.4 Hz, 1H), 7.00 (s, 1H), 6.91 (dd, J=8.1, 1.5 Hz, 1H), 6.74 (t, J=8.1 Hz, 1H), 6.27 (d, J=8.0 Hz, 1H), 4.76 (d, J=5.3 Hz, 1H), 4.27-4.09 (m, 1H), 2.80 (d, J=4.7 Hz, 3H), 1.78-1.40 (m, 16H).
LC-MS (ESI): [M+H]⁺=334.2

Example 17

N-cyclononyl-2-hydroxy-3-(2,2,2-trifluoroacetamido)benzamide

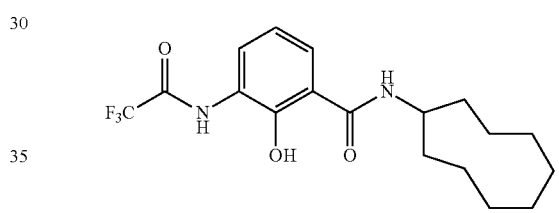

¹H NMR (300 MHz, CDCl₃) δ 13.53 (s, 1H), 8.69 (s, 1H), 8.43 (d, J=7.7 Hz, 1H), 7.17 (dd, J=8.2, 1.4 Hz, 1H), 6.88 (t, J=8.1 Hz, 1H), 6.28 (d, J=8.0 Hz, 1H), 4.35-4.17 (m, 1H), 1.89-1.54 (m, 16H).
¹⁹F NMR (282 MHz, CDCl₃) δ-75.81 (s)
LC-MS (ESI): [M+H]⁺=373.2

Example 18

2,4-dichloro-6-((cyclononylamino)methyl)phenol

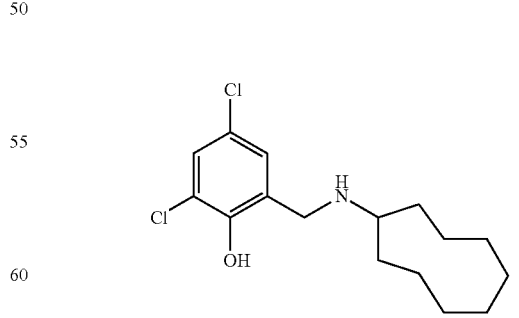

¹H NMR (300 MHz, CDCl₃) δ 7.24 (d, J=2.6 Hz, 1H), 6.87 (d, J=2.5 Hz, 1H), 4.78 (s, 1H), 3.96 (s, 2H), 2.80-2.73 (m, 1H), 1.92 (br s, 1H), 1.80-1.35 (m, 16H).
LC-MS (ESI): [M+H]⁺=316.0

Example 19

3-formamido-N-(heptadecan-9-yl)-2-hydroxybenzamide

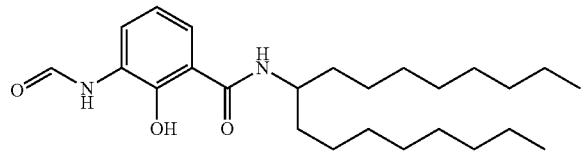 [SMILES: CCCCCCCCC(CCCCCCCC)NC(=O)c1cccc(NC=O)c1O]

$^1$H NMR (300 MHz, CDCl$_3$) δ 13.28 (s, 1H), 8.44 (dd, J=6.2, 1.6 Hz, 1H), 7.89 (s, 1H), 7.03 (dd, J=8.2, 1.4 Hz, 1H), 6.79 (t, J=8.0 Hz, 1H), 4.12-3.97 (m, 1H), 1.59-1.14 (m, 34H).

LC-MS (ESI): [M+H]$^+$=419.3

Example 20

2,4-dichloro-6-(1-hydroxyundecyl)phenol

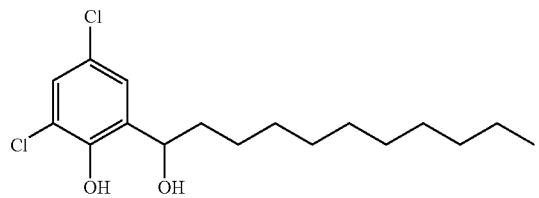 [SMILES: CCCCCCCCCCC(O)c1cc(Cl)cc(Cl)c1O]

$^1$H NMR (300 MHz, CDCl$_3$) δ 12.96 (s, 1H), 7.48 (d, J=2.3 Hz, 1H), 7.25 (d, J=2.4 Hz, 1H), 6.27 (s, 1H), 3.44 (q, J=6.8 Hz, 1H), 1.68-1.52 (m, 2H), 1.41-1.22 (m, 16H), 0.93-0.80 (m, 3H).

LC-MS (ESI): [M+H]$^+$=333.1

Example 21

3-((3-(cyclononylcarbamoyl)-2-hydroxyphenyl)amino)-3-oxopropanoic acid

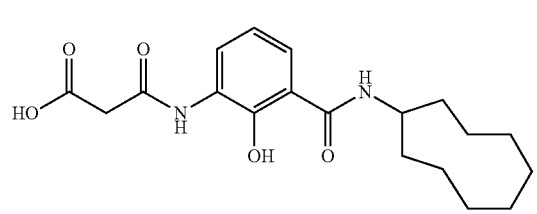 [SMILES: O=C(O)CC(=O)Nc1cccc(C(=O)NC2CCCCCCCC2)c1O]

$^1$H NMR (300 MHz, CD$_3$OD-d$_4$) δ 8.42 (d, J=7.9 Hz, 1H), 7.18 (dd, J=8.1, 1.4 Hz, 1H), 6.89 (d, J=8.0 Hz, 1H), 4.34-4.14 (m, 1H), 3.32 (s, 2H), 1.88-1.54 (m, 16H).

LC-MS (ESI): [M+H]$^+$=363.2

Example 22

N-(3,5-dichloro-2-hydroxyphenyl)undecanamide

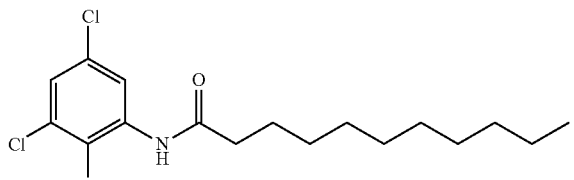

$^1$H NMR (300 MHz, CDCl$_3$) δ 7.93 (s, 1H), 7.70 (d, J=2.4 Hz, 1H), 7.68 (s, 1H), 7.11 (d, J=2.4 Hz, 1H), 2.48-2.29 (m, 2H), 1.79-1.61 (m, 2H), 1.43-1.21 (m, 14H), 0.94-0.81 (m, 3H).

LC-MS (ESI): [M+H]$^+$=346.1

Example 23

N-cyclononyl-3-formamidobenzamide

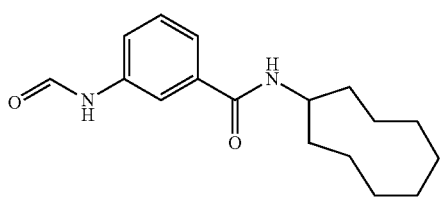 [SMILES: O=CNc1cccc(C(=O)NC2CCCCCCCC2)c1]

$^1$H NMR (300 MHz, CDCl$_3$) δ 9.26 (s, 1H), 8.35 (d, J=1.8 Hz, 1H), 7.97 (d, J=9.1 Hz, 1H), 7.54-7.17 (m, 3H), 6.42 (d, J=8.9 Hz, 1H), 4.28-4.16 (m, 1H), 1.96-1.34 (m, 16H).

LC-MS (ESI): [M+H]$^+$=289.2

Example 24

N-cyclopentadecyl-2-(3-formamido-2-hydroxyphenyl)-5-methyloxazole-4-carboxamide

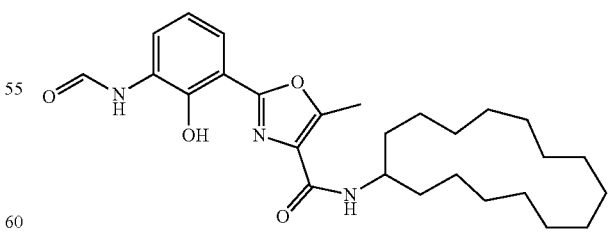

$^1$H NMR (300 MHz, CDCl$_3$) δ 10.47 (s, 1H), 7.23 (dd, J=6.0, 3.5 Hz, 1H), 6.87-6.74 (m, 2H), 6.46 (d, J=8.9 Hz, 1H), 4.18-4.05 (m, 1H), 3.93 (br s, 1H), 2.74 (s, 3H), 1.72-1.19 (m, 28H).

LC-MS (ESI): [M+H]$^+$=470.3

Example 25

N-cyclononyl-2-(3-formamido-2-hydroxyphenyl)-5-methyloxazole-4-carboxamide

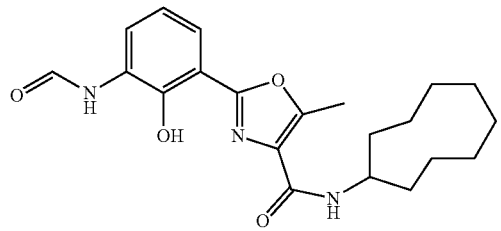 [SMILES: Cc1oc(-c2cccc(NC=O)c2O)nc1C(=O)NC1CCCCCCCC1]

$^1$H NMR (300 MHz, CDCl$_3$) δ 10.88 (s, 1H), 8.52 (s, 1H), 8.47 (d, J=8.1 Hz, 1H), 7.89 (br s, 1H), 7.57 (d, J=7.9 Hz, 1H), 6.99 (t, J=8.1 Hz, 1H), 6.55 (d, J=9.1 Hz, 1H), 4.46-4.10 (m, 1H), 2.75 (s, 3H), 1.99-1.32 (m, 16H).
LC-MS (ESI): [M+H]$^+$=386.2

Example 26

N-(2-hydroxy-3-(5-methyloxazol-2-yl)phenyl)formamide

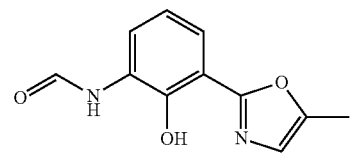 [SMILES: Cc1cnc(-c2cccc(NC=O)c2O)o1]

$^1$H NMR (300 MHz, CDCl$_3$) δ 11.81 (br s, 1H), 8.44 (d, J=1.8 Hz, 1H), 8.36 (dd, J=8.1, 1.5 Hz, 1H), 7.88 (br s, 1H), 7.47 (dd, J=7.9, 1.5 Hz, 1H), 6.88 (t, J=8.0 Hz, 1H), 6.79 (dd, J=3.0, 1.7 Hz, 1H), 2.35 (d, J=1.3 Hz, 3H).
LC-MS (ESI): [M+H]$^+$=219.1

Example 27

N-adamantan-1-yl-4-((2,5-dihydroxybenzyl)amino)benzamide

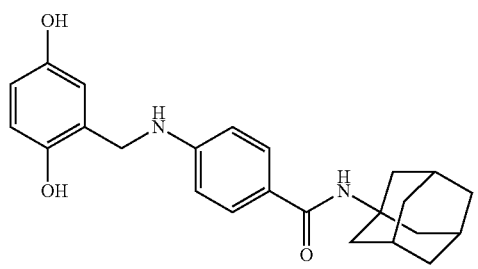 [SMILES: O=C(NC12CC3CC(CC(C3)C1)C2)c1ccc(NCc2cc(O)ccc2O)cc1]

$^1$H NMR (300 MHz, CD$_3$OD-d$_4$) δ 7.77-7.70 (m, 1H), 6.74-6.46 (m, 6H), 4.30 (s, 2H), 2.20-2.08 (m, 9H), 1.81-1.62 (m, 6H).
LC-MS (ESI): [M+H]$^+$=393.1

Example 28

N-adamantan-1-yl-4-((3,5-dichloro-2-hydroxybenzyl)amino)benzamide

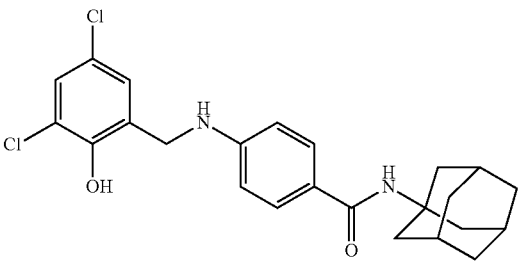 [SMILES: O=C(NC12CC3CC(CC(C3)C1)C2)c1ccc(NCc2cc(Cl)cc(Cl)c2O)cc1]

$^1$H NMR (300 MHz, DMSO-d$_6$) δ 9.74 (br s, 1H), 7.53 (d, J=8.4 Hz, 2H), 7.35 (d, J=2.6 Hz, 1H), 7.08 (s, 2H), 6.65 (br s, 1H), 6.49 (d, J=8.4 Hz, 2H), 4.28 (s, 2H), 2.15-1.90 (m, 9H), 1.66-1.54 (m, 6H).
LC-MS (ESI): [M+H]$^+$=445.0

Example 29

N-(4-(adamantan-1-ylcarbamoyl)phenyl)-3,5-dichloro-2-hydroxybenzamide

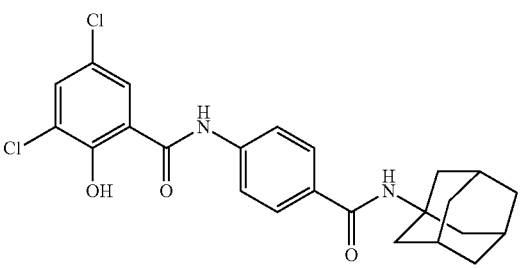 [SMILES: O=C(NC12CC3CC(CC(C3)C1)C2)c1ccc(NC(=O)c2cc(Cl)cc(Cl)c2O)cc1]

$^1$H NMR (300 MHz, CDCl$_3$) δ 10.10 (s, 1H), 7.89 (d, J=2.5 Hz, 1H), 7.47 (d, J=8.5 Hz, 2H), 7.43 (d, J=2.2 Hz, 1H), 6.57 (d, J=8.5 Hz, 2H), 5.89 (br s, 1H), 5.74 (br s, 1H), 2.16-1.92 (m, 9H), 1.72-1.59 (m, 6H).
LC-MS (ESI): [M+H]$^+$=459.1

Example 30

N-(4-(adamantan-1-ylcarbamoyl)phenyl)-3-formamido-2-hydroxybenzamide

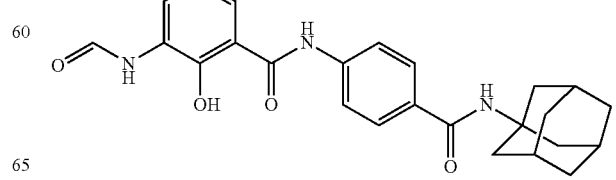

¹H NMR (300 MHz, CDCl₃) δ 9.42 (s, 1H), 7.71-7.60 (m, 1H), 7.52 (d, J=8.5 Hz, 2H), 7.42-7.21 (m, 3H), 6.61 (d, J=8.5 Hz, 2H), 5.69 (s, 1H), 4.95 (s, 1H), 2.21-2.01 (m, 9H), 1.80-1.60 (m, 6H).
LC-MS (ESI): [M+H]⁺=434.1

Example 31

N-(4-(cyclononylcarbamoyl)phenyl)-3-formamido-2-hydroxybenzamide

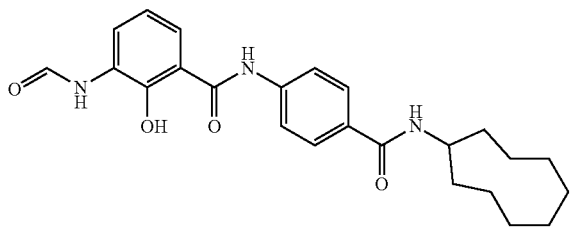 [SMILES: O=CNc1cccc(C(=O)Nc2ccc(C(=O)NC3CCCCCCCC3)cc2)c1O]

¹H NMR (300 MHz, CDCl₃) δ 12.53 (s, 1H), 8.46 (dd, J=5.9, 1.5 Hz, 1H), 8.16 (s, 1H), 7.89 (br s, 1H), 7.72 (d, J=8.6 Hz, 2H), 7.61 (d, J=8.6 Hz, 2H), 7.27 (dd, J=8.2, 1.1 Hz, 1H), 6.89 (t, J=8.1 Hz, 1H), 5.92 (br s, 1H), 4.25-4.10 (m, 1H), 1.80-1.40 (m, 16H).
LC-MS (ESI): [M+H]⁺=424.2

Example 32

N-(4-(cyclopentadecylcarbamoyl)phenyl)-3-formamido-2-hydroxybenzamide

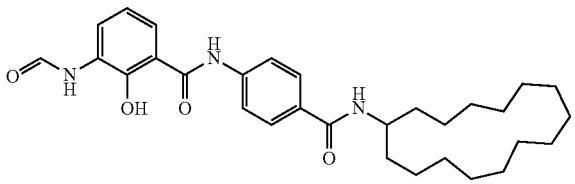 [SMILES: O=CNc1cccc(C(=O)Nc2ccc(C(=O)NC3CCCCCCCCCCCCCC3)cc2)c1O]

¹H NMR (300 MHz, CDCl₃) δ 12.56 (s, 1H), 8.45 (dd, J=6.5, 2.4 Hz, 1H), 7.93 (s, 1H), 7.70 (d, J=8.6 Hz, 2H), 7.62 (d, J=8.5 Hz, 2H), 7.34 (d, J=8.1 Hz, 1H), 7.19 (s, 1H), 6.84 (t, J=8.0 Hz, 1H), 5.85 (d, J=8.5 Hz, 1H), 4.16-4.03 (m, 1H), 1.65-1.24 (m, 28H).
LC-MS (ESI): [M+H]⁺=508.3

Example 33

N-(3-(5-cyclononyloxazol-2-yl)-2-hydroxyphenyl)formamide

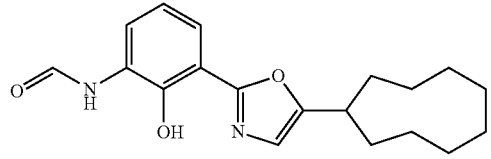 [SMILES: O=CNc1cccc(-c2ncc(C3CCCCCCCC3)o2)c1O]

Example 34

N-(2-hydroxy-3-(5-nonyloxazol-2-yl)phenyl)formamide

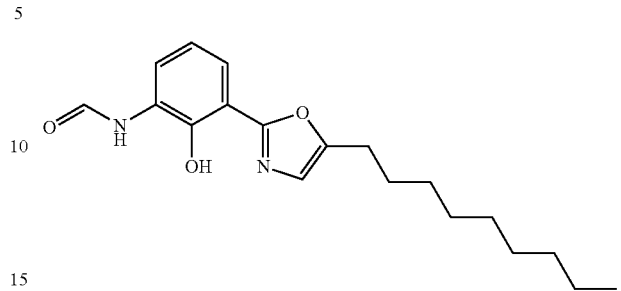

Example 35

N-(4-(4-cyclononyl-5-methyloxazol-2-yl)-2-hydroxyphenyl)formamide

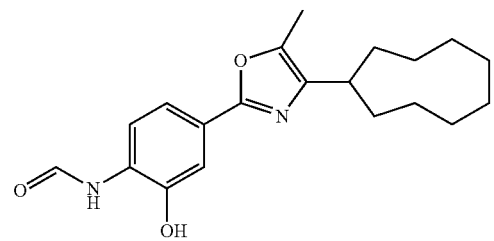 [SMILES: Cc1oc(-c2ccc(NC=O)c(O)c2)nc1C1CCCCCCCC1]

Example 36

N-(2-hydroxy-4-(5-methyl-4-nonyloxazol-2-yl)phenyl)formamide

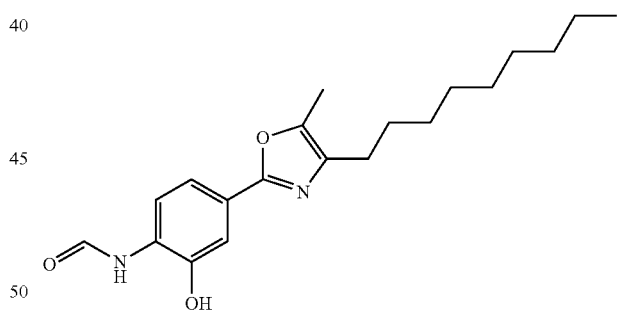

Example 37

N-(3-(2-cyclononyloxazol-5-yl)-2-hydroxyphenyl)formamide

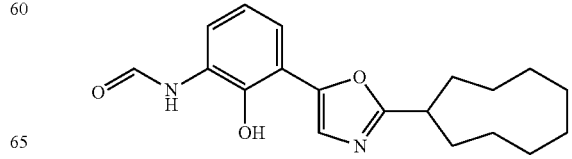

Example 38

N-(2-hydroxy-3-(2-nonyloxazol-5-yl)phenyl)formamide

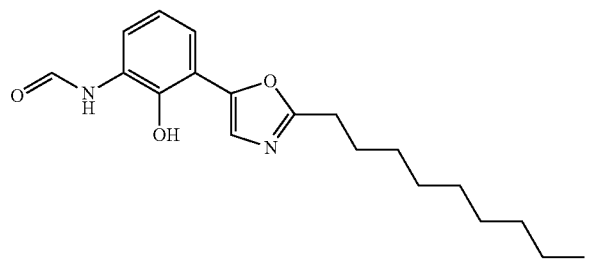 [SMILES: CCCCCCCCCc1ncc(-c2cccc(NC=O)c2O)o1]

Example 39

N-(4-(2-cyclononyloxazol-5-yl)-2-hydroxyphenyl)formamide

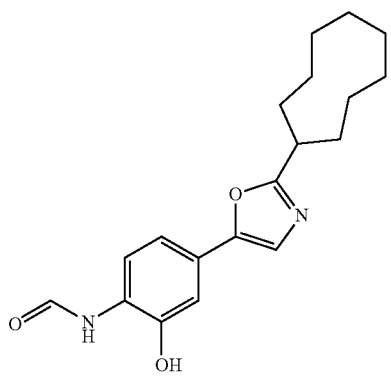 [SMILES: O=CNc1ccc(-c2cnc(C3CCCCCCCC3)o2)cc1O]

Example 40

N-(2-hydroxy-4-(2-nonyloxazol-5-yl)phenyl)formamide

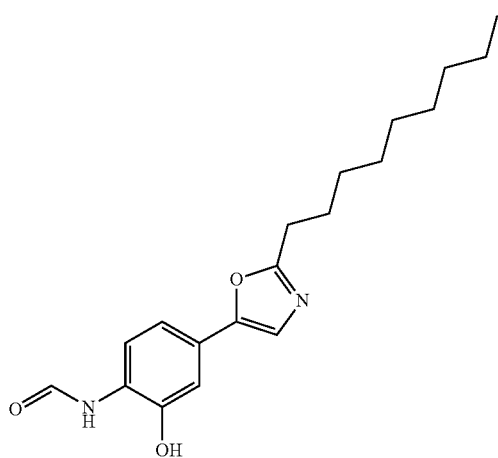 [SMILES: CCCCCCCCCc1ncc(-c2ccc(NC=O)c(O)c2)o1]

Example 41

N-(2-hydroxy-3-(3-nonyloxetan-3-yl)phenyl)formamide

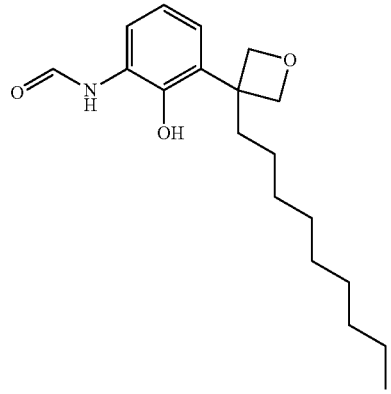 [SMILES: CCCCCCCCCC1(c2cccc(NC=O)c2O)COC1]

Example 42

N-benzyl-N-cyclononyl-3-formamido-2-hydroxybenzamide

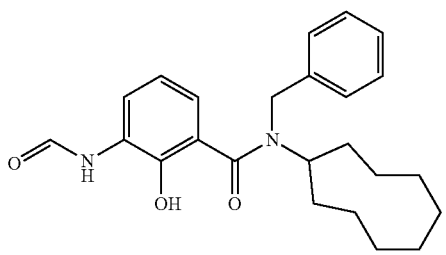 [SMILES: O=CNc1cccc(C(=O)N(Cc2ccccc2)C2CCCCCCCC2)c1O]

Example 43

N-cyclononyl-3-formamido-2,5-dihydroxybenzamide

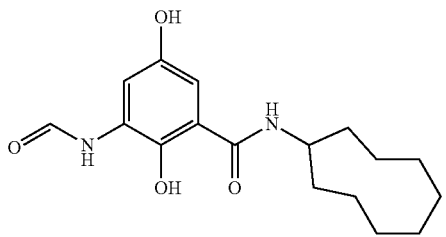 [SMILES: O=CNc1cc(O)cc(C(=O)NC2CCCCCCCC2)c1O]

Example 44

5-chloro-N-cyclononyl-3-formamido-2-hydroxybenzamide

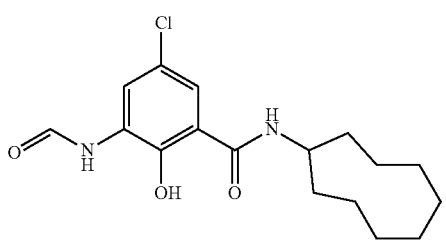 [SMILES: O=CNc1cc(C(F)(F)F)cc(C(=O)NC2CCCCCCCC2)c1O]

Example 45

N-cyclononyl-3-formamido-2-hydroxy-5-(trifluoromethyl)benzamide

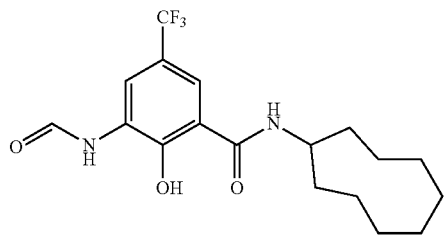

Example 46

3-formamido-2-hydroxy-N-(1-octanamido-2,3-dihydro-1H-inden-2-yl)benzamide

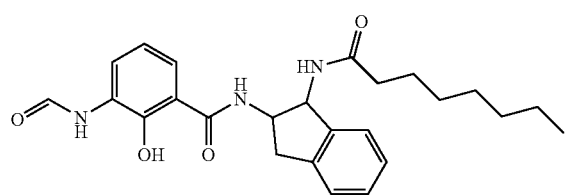 [SMILES: CCCCCCCC(=O)NC1c2ccccc2CC1NC(=O)c1cccc(NC=O)c1O]

Example 47

3-formamido-2,5-dihydroxy-N-(1-octanamido-2,3-dihydro-1H-inden-2-yl)benzamide

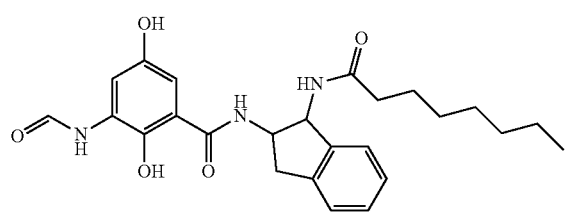 [SMILES: CCCCCCCC(=O)NC1c2ccccc2CC1NC(=O)c1cc(O)cc(NC=O)c1O]

Example 48

5-chloro-3-formamido-2-hydroxy-N-(1-octanamido-2,3-dihydro-1H-inden-2-yl)benzamide

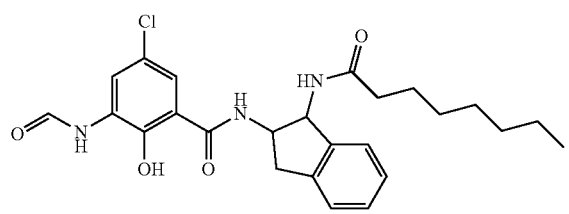 [SMILES: CCCCCCCC(=O)NC1c2ccccc2CC1NC(=O)c1cc(Cl)cc(NC=O)c1O]

Example 49

3-formamido-2-hydroxy-N-(1-octanamido-2,3-dihydro-1H-inden-2-yl)-5-(trifluoromethyl)benzamide

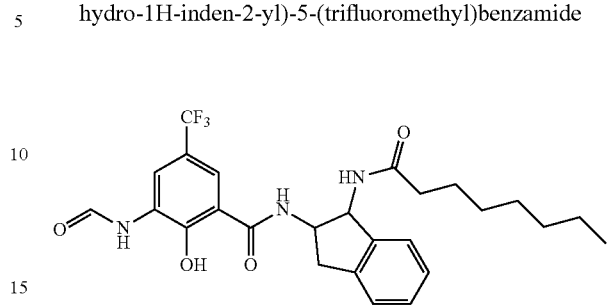

Example 50

N-(3-decanoyl-2-hydroxyphenyl)formamide

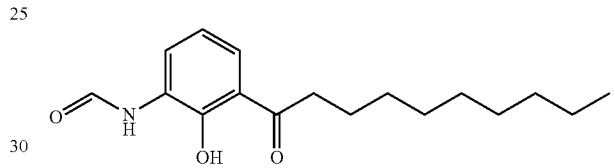

Example 51

(E)-N-(2-hydroxy-3-(1-(hydroxyimino)decyl)phenyl)formamide

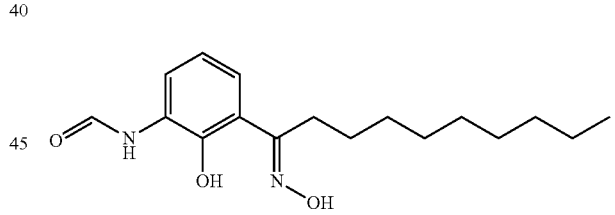

Example 52

(E)-N-(2-hydroxy-3-(1-(methoxyimino)decyl)phenyl)formamide

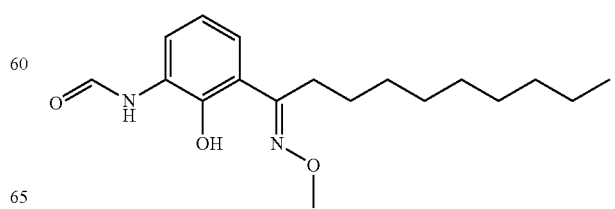

Example 53

(E)-N-(2-hydroxy-3-(1-methoxyundec-1-en-2-yl)phenyl)formamide

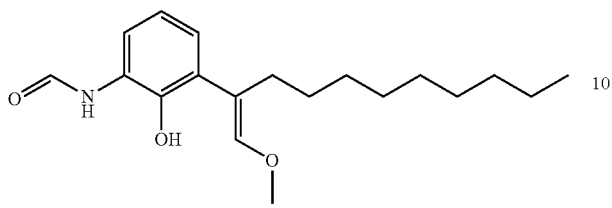

Example 54

1-(3,5-dichloro-2-hydroxyphenyl)decan-1-one

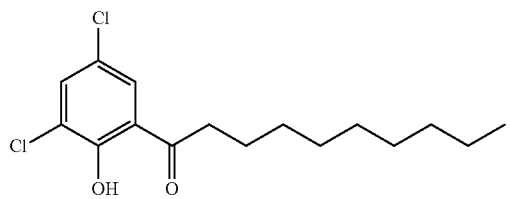 [SMILES: CCCCCCCCCC(=O)c1cc(Cl)cc(Cl)c1O]

Example 55

(E)-1-(3,5-dichloro-2-hydroxyphenyl)decan-1-one oxime

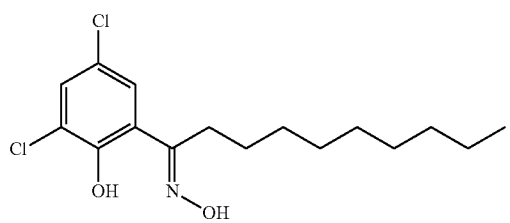 [SMILES: CCCCCCCCC/C(=N\O)c1cc(Cl)cc(Cl)c1O]

Example 56

(E)-1-(3,5-dichloro-2-hydroxyphenyl)decan-1-one O-methyl oxime

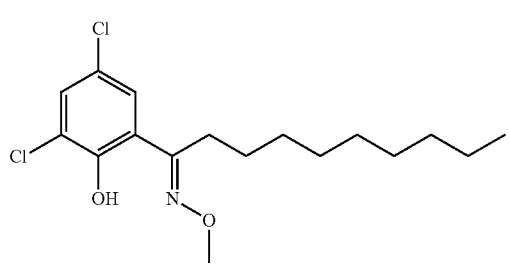 [SMILES: CCCCCCCCC/C(=N\OC)c1cc(Cl)cc(Cl)c1O]

Example 57

(E)-2,4-dichloro-6-(1-methoxyundec-1-en-2-yl)phenol

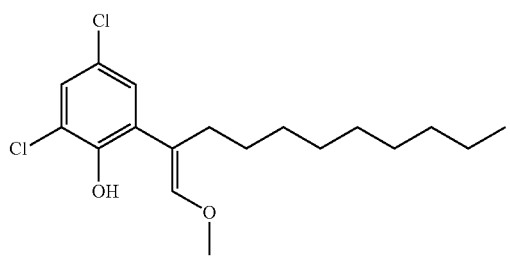 [SMILES: CCCCCCCCC/C(=C\OC)c1cc(Cl)cc(Cl)c1O]

Example 58

2-(3-formamido-2-hydroxyphenyl)-N-nonyloxazole-4-carboxamide

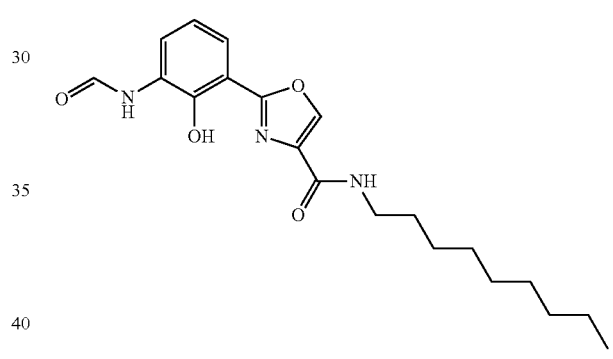

Example 59

N-cyclononyl-2-(3-formamido-2-hydroxyphenyl)oxazole-4-carboxamide

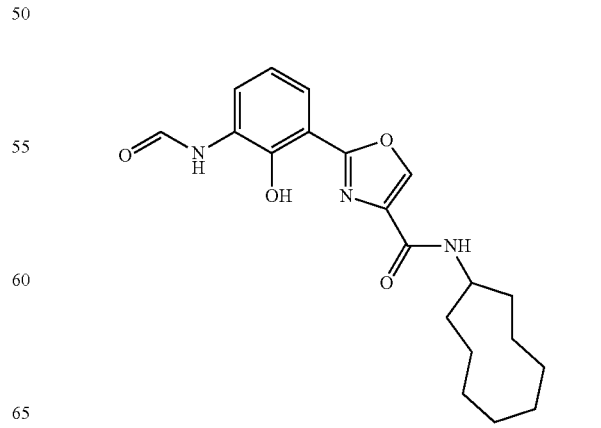

33

Example 60

N-cyclopentadecyl-2-(3-formamido-2-hydroxyphenyl)oxazole-4-carboxamide

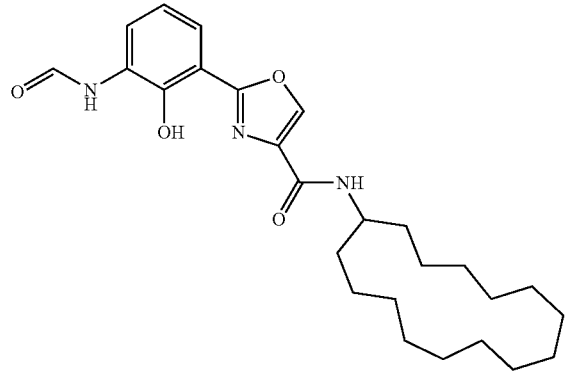 [SMILES: O=CNc1cccc(-c2nc(C(=O)NC3CCCCCCCCCCCCCC3)co2)c1O]

Example 61

2-(3-formamido-2-hydroxyphenyl)-N-nonylthiazole-4-carboxamide

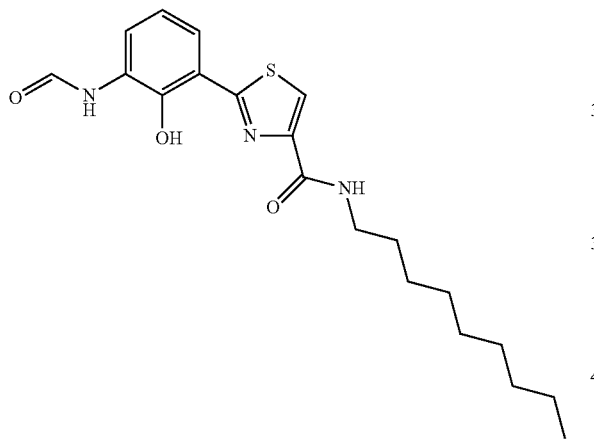

Example 62

N-cyclononyl-2-(3-formamido-2-hydroxyphenyl)thiazole-4-carboxamide

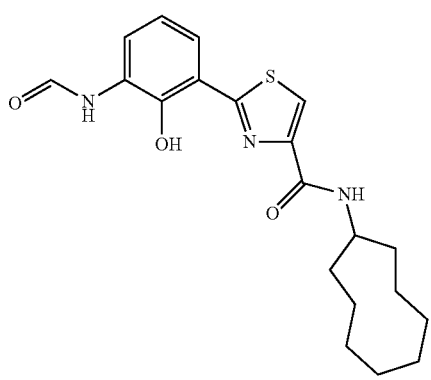 [SMILES: O=CNc1cccc(-c2nc(C(=O)NC3CCCCCCCC3)cs2)c1O]

34

Example 63

N-cyclopentadecyl-2-(3-formamido-2-hydroxyphenyl)thiazole-4-carboxamide

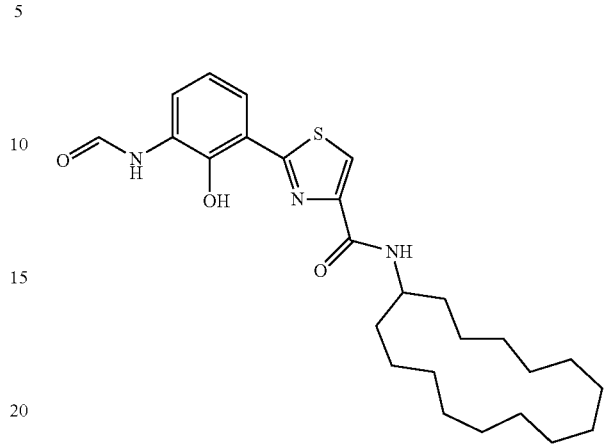

Example 64

5-(3-formamido-2-hydroxyphenyl)-N-nonyloxazole-2-carboxamide

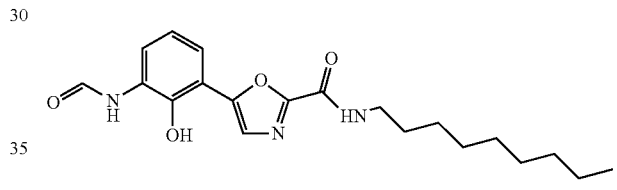

Example 65

N-cyclononyl-5-(3-formamido-2-hydroxyphenyl)oxazole-2-carboxamide

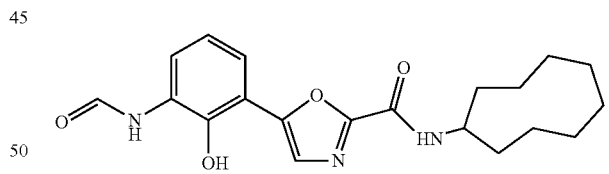

Example 66

N-cyclopentadecyl-5-(3-formamido-2-hydroxyphenyl)oxazole-2-carboxamide

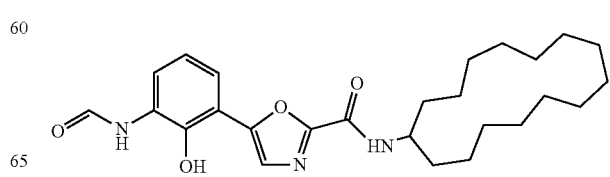

Example 67

5-(3-formamido-2-hydroxyphenyl)-N-nonylthiazole-2-carboxamide

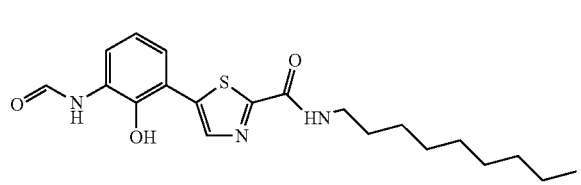 [SMILES: CCCCCCCCCNC(=O)c1ncc(-c2cccc(NC=O)c2O)o1]

Example 68

N-cyclononyl-5-(3-formamido-2-hydroxyphenyl)thiazole-2-carboxamide

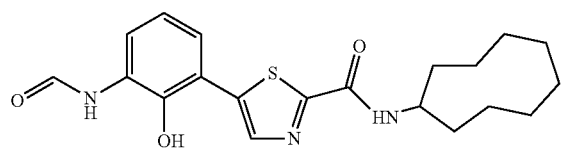 [SMILES: O=CNc1cccc(-c2cnc(C(=O)NC3CCCCCCCC3)o2)c1O]

Example 69

N-cyclopentadecyl-5-(3-formamido-2-hydroxyphenyl)thiazole-2-carboxamide

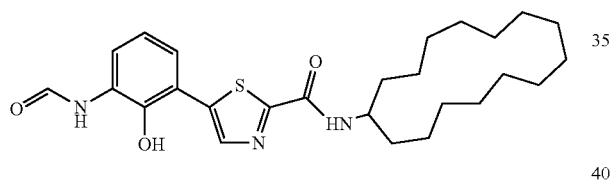

Example 70

N-(2-hydroxy-3-(4-nonylisoxazol-3-yl)phenyl)formamide

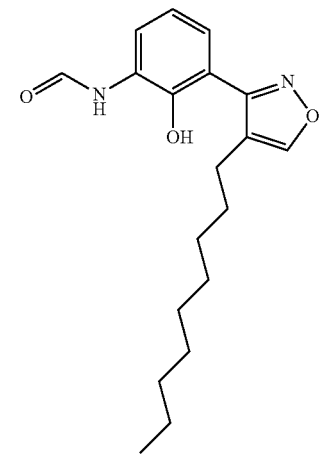 [SMILES: CCCCCCCCCc1conc1-c1cccc(NC=O)c1O]

Example 71

N-(3-(4-(cyclononylmethyl)isoxazol-3-yl)-2-hydroxyphenyl)formamide

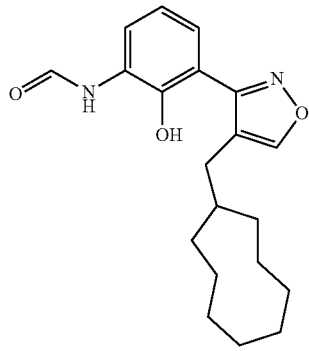 [SMILES: O=CNc1cccc(-c2nocc2CC2CCCCCCCC2)c1O]

Example 72

N-(2-hydroxy-3-(3-(nonylamino)oxetan-3-yl)phenyl)formamide

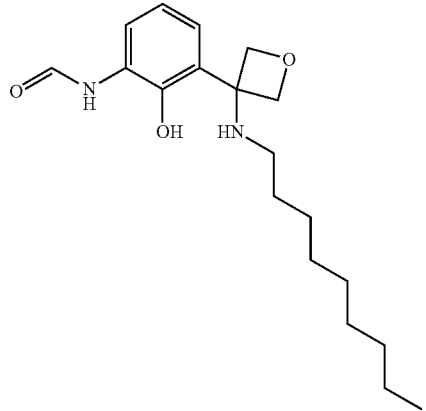 [SMILES: CCCCCCCCCNC1(c2cccc(NC=O)c2O)COC1]

Example 74

2-(5-chloro-3-formamido-2-hydroxyphenyl)-N-nonyloxazole-4-carboxamide

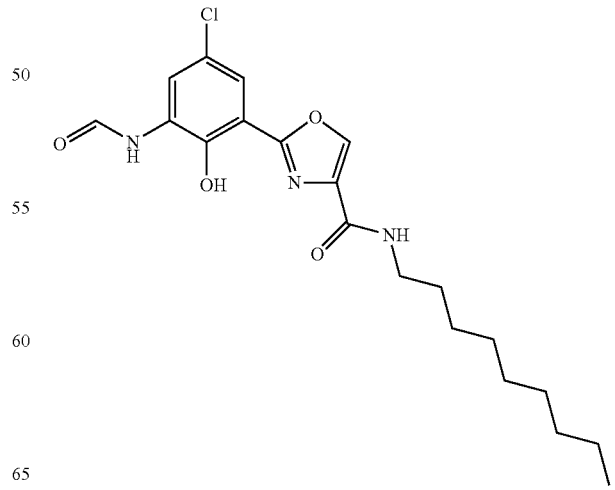

Example 75

2-(5-chloro-3-formamido-2-hydroxyphenyl)-N-cyclononyloxazole-4-carboxamide

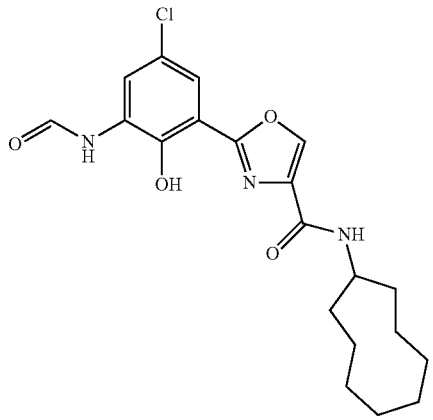 [SMILES: O=CNc1cc(Cl)cc(-c2nc(C(=O)NC3CCCCCCCC3)co2)c1O]

Example 76

2-(5-chloro-3-formamido-2-hydroxyphenyl)-N-cyclopentadecyloxazole-4-carboxamide

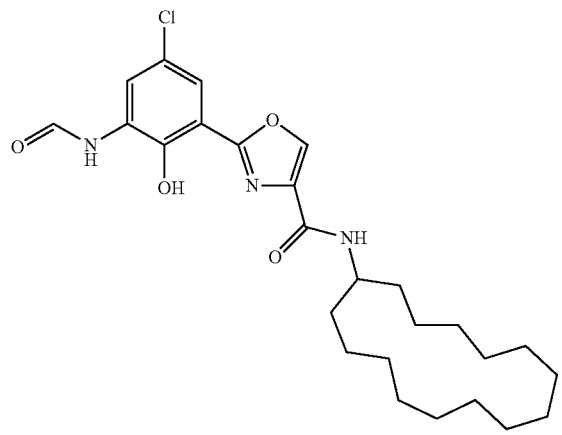 [SMILES: O=CNc1cc(Cl)cc(-c2nc(C(=O)NC3CCCCCCCCCCCCCC3)co2)c1O]

Example 77

2-(3-formamido-2-hydroxy-5-(trifluoromethyl)phenyl)-N-nonyloxazole-4-carboxamide

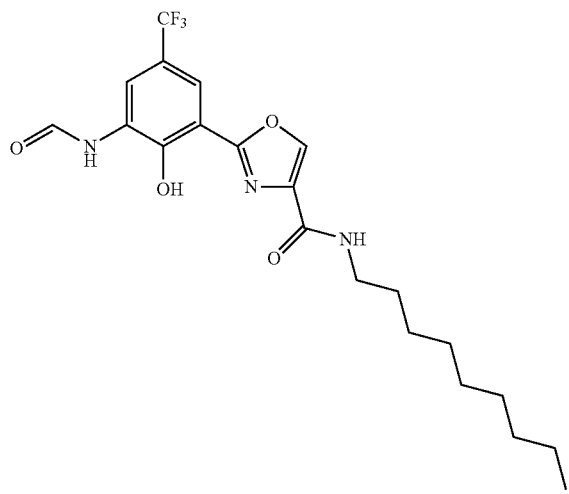 [SMILES: CCCCCCCCCNC(=O)c1coc(-c2cc(C(F)(F)F)cc(NC=O)c2O)n1]

Example 78

N-cyclononyl-2-(3-formamido-2-hydroxy-5-(trifluoromethyl)phenyl)oxazole-4-carboxamide

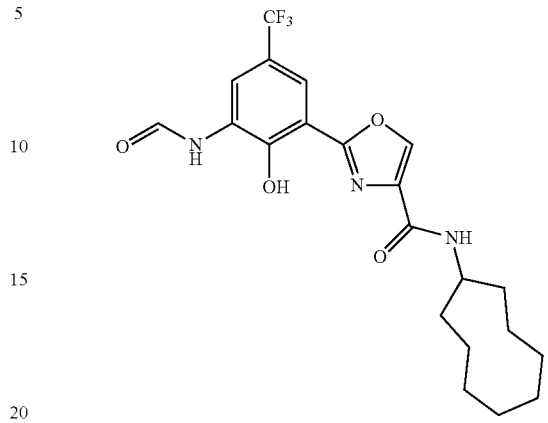

Example 79

N-cyclopentadecyl-2-(3-formamido-2-hydroxy-5-(trifluoromethyl)phenyl)oxazole-4-carboxamide

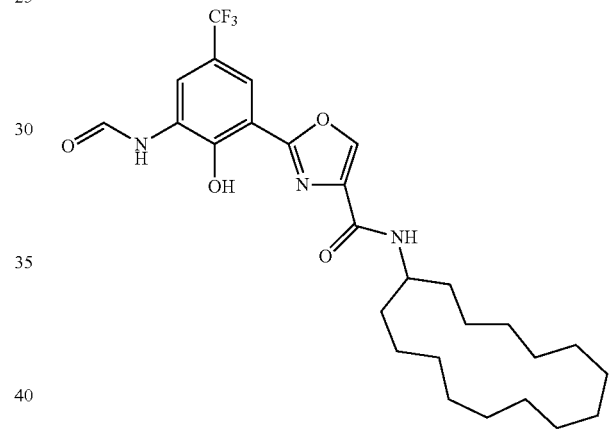

Example 80

2-(3-formamido-5-formyl-2-hydroxyphenyl)-N-nonyloxazole-4-carboxamide

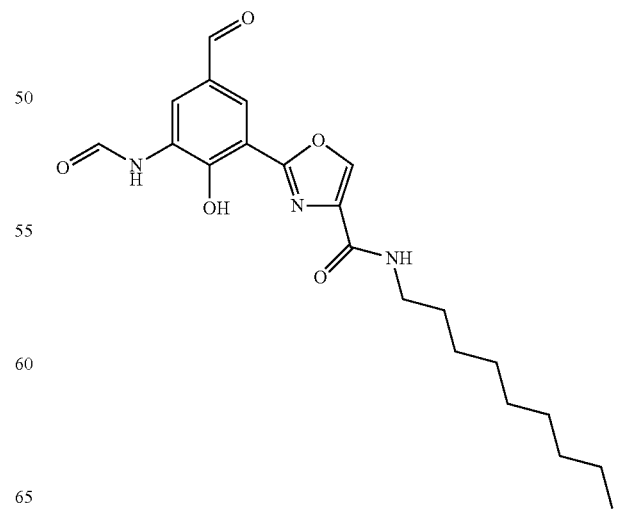

Example 81

N-cyclononyl-2-(3-formamido-5-formyl-2-hydroxy-phenyl)oxazole-4-carboxamide

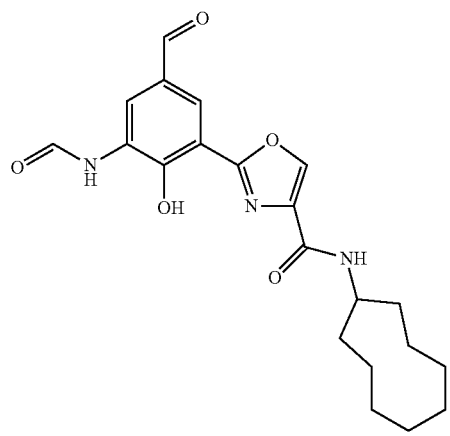 [SMILES: O=CNc1cc(C=O)cc(-c2nc(C(=O)NC3CCCCCCCC3)co2)c1O]

Example 82

N-cyclopentadecyl-2-(3-formamido-5-formyl-2-hydroxyphenyl)oxazole-4-carboxamide

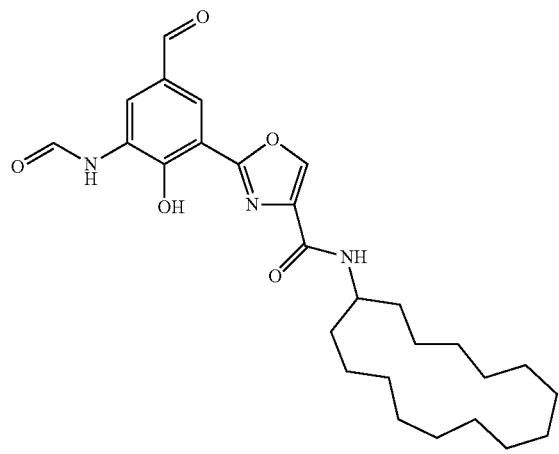 [SMILES: O=CNc1cc(C=O)cc(-c2nc(C(=O)NC3CCCCCCCCCCCCCC3)co2)c1O]

Example 83

N-(3-((2-(cyclononylamino)-3,4-dioxocyclobut-1-en-1-yl)amino)-2-hydroxyphenyl)formamide

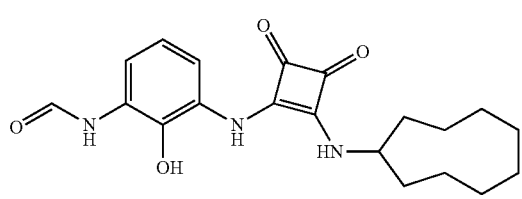 [SMILES: O=CNc1cccc(Nc2c(NC3CCCCCCCC3)c(=O)c2=O)c1O]

Example 84

N-(3-((2-(cyclononylamino)-3,4-dioxocyclobut-1-en-1-yl)oxy)-2-hydroxyphenyl)formamide

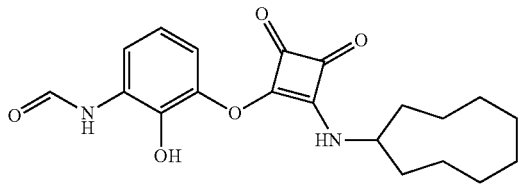 [SMILES: O=CNc1cccc(Oc2c(NC3CCCCCCCC3)c(=O)c2=O)c1O]

Example 85

N-(3-(2-(cyclononylamino)-3,4-dioxocyclobut-1-en-1-yl)-2-hydroxyphenyl)formamide

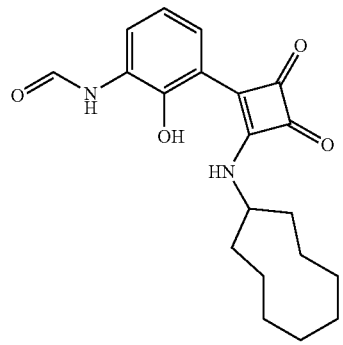 [SMILES: O=CNc1cccc(-c2c(NC3CCCCCCCC3)c(=O)c2=O)c1O]

Example 86

N-(-2-hydroxy-3-(5-(2-oxo-4-phenylbutyl)oxazol-2-yl)phenyl)formamide

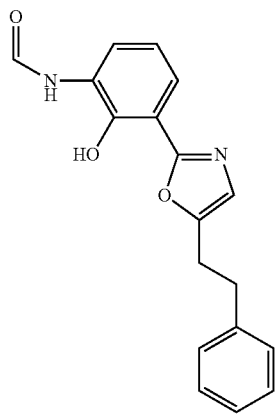 [SMILES: O=CNc1cccc(-c2ncc(CCc3ccccc3)o2)c1O]

$^1$H NMR (300 MHz, Chloroform-d) δ 8.77-8.32 (m, 2H), 7.88 (s, 1H), 7.49 (ddd, J=15.8, 7.9, 1.5 Hz, 1H), 7.29-7.08 (m, 5H), 6.88 (t, J=8.1 Hz, 1H), 6.73 (s, 1H), 3.07-2.89 (m, 4H).

LC-MS (ESI): [M+H]$^+$=309.1

Example 87

N-(2-hydroxy-3-(5-(2-oxo-4-phenylbutyl)oxazol-2-yl)phenyl)formamide

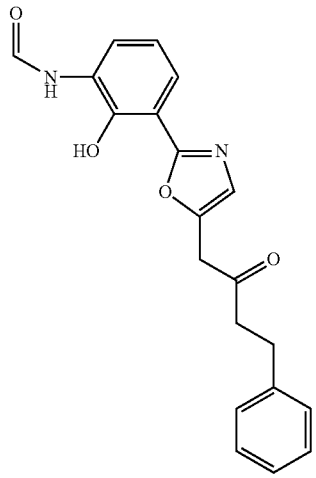 [SMILES: O=CNc1cccc(-c2ncc(CC(=O)CCc3ccccc3)o2)c1O]

$^1$H NMR (300 MHz, Chloroform-d) δ 8.79-8.34 (m, 2H), 7.46 (ddd, J=15.9, 8.0, 1.5 Hz, 1H), 7.26-7.07 (m, 5H), 7.00 (s, 1H), 6.88 (t, J=8.0 Hz, 1H), 3.77 (d, J=0.9 Hz, 2H), 2.96-2.74 (m, 4H).

LC-MS (ESI): [M+H]$^+$=351.1

Example 88

N-(2-(1H-benzo[d]imidatol-2-yl)phenyl)formamide

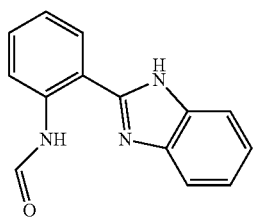 [SMILES: O=CNc1ccccc1-c1nc2ccccc2[nH]1]

$^1$H NMR (300 MHz, Chloroform-d) δ 9.13 (s, 1H), 8.67 (dd, J=7.9, 1.6 Hz, 1H), 8.06-7.89 (m, 3H), 7.85-7.74 (m, 1H), 7.74-7.65 (m, 1H), 7.58 (ddd, J=8.2, 7.2, 1.2 Hz, 1H), 7.53-7.43 (m, 1H).

LC-MS (ESI): [M+H]$^+$=238.1

Example 89

N-(2-(5,6-dimethyl-1H-benzo[d]imidazole-2-yl)phenyl)formamide

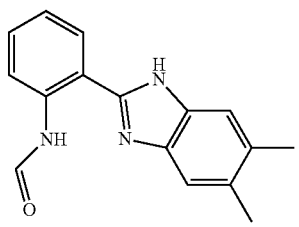 [SMILES: Cc1cc2nc(-c3ccccc3NC=O)[nH]c2cc1C]

$^1$H NMR (300 MHz, Chloroform-d) δ 9.12 (s, 1H), 8.65 (dd, J=8.0, 1.5 Hz, 1H), 7.97 (dd, J=8.2, 1.2 Hz, 1H), 7.87-7.57 (m, 5H), 2.45 (d, J=3.2 Hz, 8H).

LC-MS (ESI): [M+H]$^+$=266.2

Example 90

N-(heptadecan-9-yl)-7-hydroxy-1H-indazole-6-carboxamide

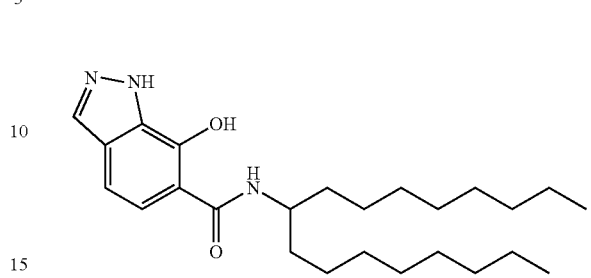

$^1$H NMR (300 MHz, Chloroform-d) δ 13.60-13.51 (bs, 1H), 10.67-10.41 (bs, 1H), 7.97 (s, 1H), 7.14 (d, J=8.5 Hz, 1H), 6.98 (d, J=8.7 Hz, 1H), 5.92 (d, J=9.0 Hz, 1H), 4.18-3.99 (m, 1H), 1.52 (m, 3H), 1.35-1.11 (m, 28H), 0.87-0.70 (m, 6H).

LC-MS (ESI): [M+H]$^+$=416.2

Example 91

3,5-dichloro-N-(heptadecane-9-yl)-2-hydroxybenzamide

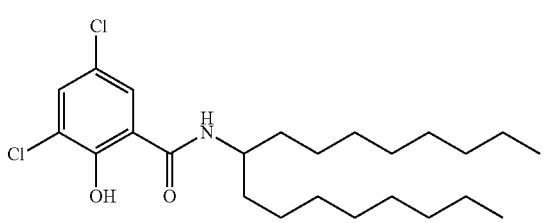 [SMILES: CCCCCCCCC(CCCCCCCC)NC(=O)c1cc(Cl)cc(Cl)c1O]

$^1$H NMR (300 MHz, Chloroform-d) δ 7.42 (d, J=2.2 Hz, 1H), 7.20-7.17 (m, 1H), 5.92 (d, J=9.0 Hz, 1H), 4.04 (ddd, J=12.7, 5.4, 2.6 Hz, 1H), 1.65-1.09 (m, 37H), 0.92-0.66 (m, 8H).

LC-MS (ESI): [M]=444.1 (92% purity)

Example 92

N-cyclopentadecyl-7-hydroxy-1H-indazole-6-carboxamide

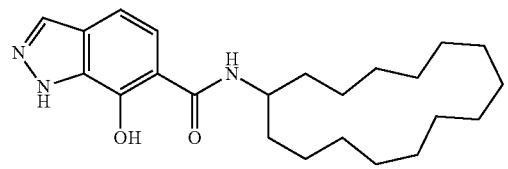 [SMILES: O=C(NC1CCCCCCCCCCCCCC1)c1ccc2cn[nH]c2c1O]

$^1$H NMR (300 MHz, CDCl$_3$) δ 13.71 (s, 1H), 11.57 (s, 1H), 8.07 (s, 1H), 7.19 (d, J=8.5 Hz, 1H), 7.05 (d, J=8.6 Hz, 1H), 6.19 (d, J=8.5 Hz, 1H), 4.20 (q, J=6.8 Hz, 1H), 1.71-1.25 (m, 28H).

LC-MS (ESI): [M+H]$^+$=386.3

Example 93

3,5-dichloro-N-(3-(3-chloro-10,11-dihydro-5H-dibenzo[b,f]azepin-5-yl)propyl)-2-hydroxybenzamide

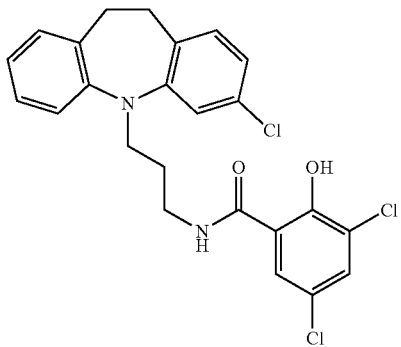 [SMILES: O=C(NCCCN1c2ccccc2CCc2ccc(Cl)cc21)c1cc(Cl)cc(Cl)c1O]

¹H NMR (300 MHz, Chloroform-d) δ 7.38 (d, J=2.4 Hz, 1H), 7.08 (m, 2H), 7.03-6.89 (m, 6H), 6.82 (dd, J=8.1, 1.9 Hz, 1H), 6.23 (t, J=5.6 Hz, 1H), 3.74 (t, J=6.4 Hz, 2H), 3.41 (td, J=7.0, 5.7 Hz, 2H), 3.04 (d, J=2.0 Hz, 4H), 1.85 (p, J=6.7 Hz, 3H).
LC-MS (ESI): [M+H]+=474.4

Example 94

N-(3-(3-chloro-10,11-dihydro-5H-dibenzo[b,f]azepin-5-yl)-3-formamido-2-hydroxybenzamide and
N-(3-(10,11-dihydro-5H-dibenzo[b,f]azepin-5-yl)-3-formamido-2-hydroxybenzamide

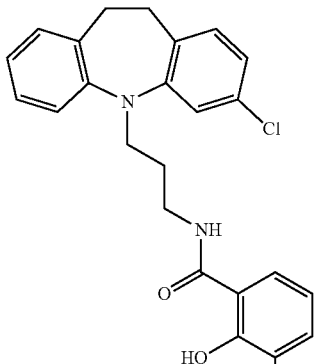

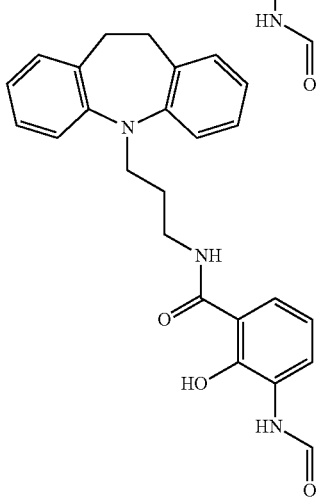

¹H NMR (300 MHz, Chloroform-d) δ 7.15-6.40 (m, 23H), 3.87-3.67 (m, 5H), 3.49-3.33 (m, 4H), 3.08 (d, J=11.7 Hz, 8H), 1.92-1.78 (m, 3H).
LC-MS (ESI): [M+H]+=449.9 (with Cl) and 416.2 (without Cl)

Example 95

N-(3-(benzo[d]oxazol-2-yl)-2-hydroxyphenyl)formamide

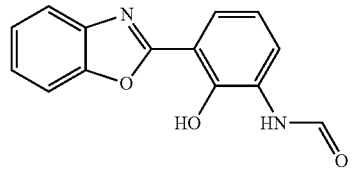 [SMILES: O=CNc1cccc(-c2nc3ccccc3o2)c1O]

¹H NMR (300 MHz, Chloroform-d) δ 11.98 (s, 1H), 8.49 (dd, J=8.0, 1.5 Hz, 1H), 7.86 (s, 1H), 7.72-7.64 (m, 2H), 7.59-7.52 (m, 1H), 7.37-7.29 (m, 2H), 6.96 (t, J=8.1 Hz, 1H).
LC-MS (ESI): [M]=254

Example 96

N-(heptadecan-9-yl)-2-oxo-2,3-dihydro-1H-benzo[d]imidazole-4-carboxamide

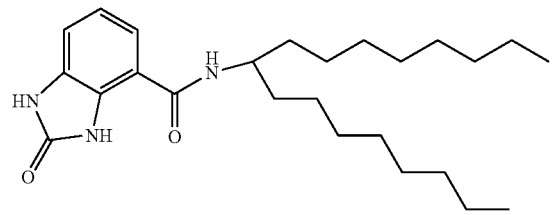 [SMILES: CCCCCCCCC(CCCCCCCC)NC(=O)c1cccc2[nH]c(=O)[nH]c12]

¹H NMR (300 MHz, Chloroform-d) δ 7.16 (dd, J=12.5, 7.8 Hz, 2H), 7.03 (t, J=7.8 Hz, 1H), 5.99 (d, J=9.0 Hz, 1H), 4.23-4.03 (m, 1H), 1.95 (d, J=4.8 Hz, 1H), 1.70-1.11 (m, 46H), 0.85 (td, J=6.6, 4.2 Hz, 10H).
LC-MS (ESI): [M+H]+=416.2

Example 97

N-(3-(3-chloro-10,11-dihydro-5H-dibenzo[b,f]azepin-5-yn)propyl)-7-hydroxy-1H-imidazole-6-carboxamide

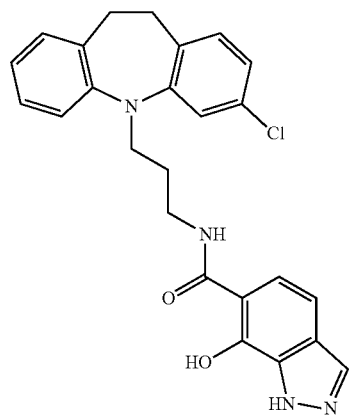 [SMILES: O=C(NCCCN1c2ccccc2CCc2ccc(Cl)cc21)c1ccc2cn[nH]c2c1O]

¹H NMR (300 MHz, Chloroform-d) δ 7.94 (s, 1H), 7.14-6.87 (m, 8H), 6.85-6.74 (m, 2H), 6.32 (t, J=5.8 Hz, 1H), 3.76 (t, J=6.5 Hz, 2H), 3.50-3.41 (m, 2H), 3.05 (d, J=2.5 Hz, 3H), 1.87 (p, J=6.7 Hz, 2H).
LC-MS (ESI): [M+H]⁺=447.1

Example 98

N-(3-(3-chloro-10,11-dihydro-5H-dibenzo[b,f]azepin-5-yl)propyl)-3-formamido-2-hydroxybenzamide

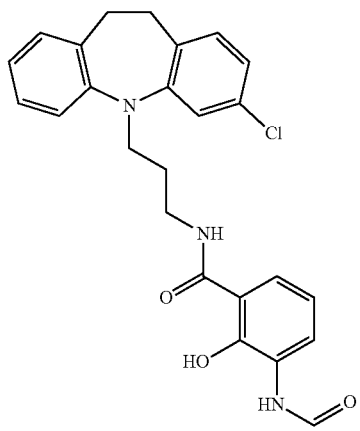 [SMILES: O=CNc1cccc(C(=O)NCCCN2c3ccccc3CCc3ccc(Cl)cc32)c1O]

¹H NMR (300 MHz, Chloroform-d) δ 13.04 (s, 1H), 8.39 (td, J=3.8, 1.4 Hz, 2H), 7.84 (s, 1H), 7.14-6.79 (m, 9H), 6.71 (t, J=8.1 Hz, 1H), 6.29 (d, J=6.0 Hz, 1H), 3.75 (t, J=6.5 Hz, 2H), 3.47-3.37 (m, 2H), 3.05 (q, J=2.6 Hz, 4H), 1.86 (p, J=6.7 Hz, 2H).
LC-MS (ESI): [M+H]⁺=450.0

Example 99

N-(3-(10,11-dihydro-5H-dibenzo[b,f]azepin-5-yl)propyl)-3-formamido-2-hydroxybenzamide

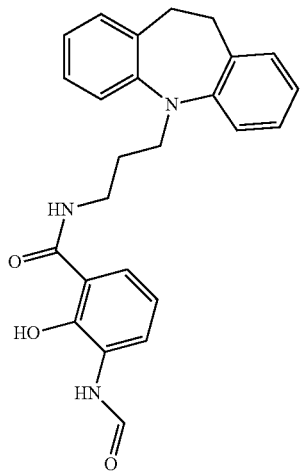 [SMILES: O=CNc1cccc(C(=O)NCCCN2c3ccccc3CCc3ccccc32)c1O]

¹H NMR (300 MHz, DMSO-d₆) δ 9.69 (d, J=1.9 Hz, 1H), 8.94 (t, J=5.4 Hz, 1H), 8.39-8.12 (m, 2H), 7.53 (dd, J=8.2, 1.5 Hz, 1H), 7.20-6.99 (m, 7H), 6.89 (dt, J=8.4, 3.8 Hz, 2H), 6.80 (t, J=8.0 Hz, 1H), 3.75 (t, J=6.7 Hz, 2H), 3.31 (s, 8H), 3.08 (s, 4H), 1.75 (p, J=6.9 Hz, 2H).
LC-MS (ESI): [M+H]⁺=416.0

Example 100

N-(3-(1-(heptadecan-9-yl)-1H-1,2,3-triazol-4-yl)-2-hydroxyphenyl)formamide

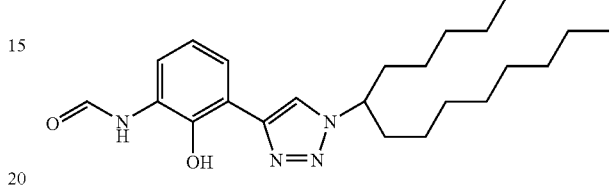

¹H NMR (300 MHz, Chloroform-d) δ 11.58 (d, J=20.1 Hz, 1H), 8.52 (d, J=1.7 Hz, 1H), 8.34 (dd, J=8.1, 1.5 Hz, 1H), 8.02 (s, 1H), 7.79 (s, 1H), 7.20 (dd, J=7.9, 1.6 Hz, 1H), 6.92 (t, J=8.0 Hz, 1H), 4.54 (p, J=7.6 Hz, 1H), 1.90 (dd, J=9.1, 5.7 Hz, 4H), 1.34-1.14 (m, 23H), 0.85 (t, J=6.6 Hz, 5H).
LC-MS (ESI): [M+H]⁺=443.1

Example 101

N-(3-(1-cyclopentadecyl-1H-1,2,3-triazol-4-yl)-2-hydroxyphenyl)formamide

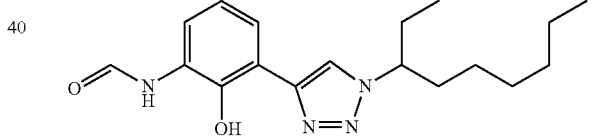

¹H NMR (300 MHz, Chloroform-d) δ 11.6-11.5 (bs, 1H), 7.88-7.76 (m, 2H), 7.31 (d, J=8.2 Hz, 1H), 7.19 (dd, J=7.8, 1.6 Hz, 1H), 4.85-4.62 (m, 2H), 2.43 (s, 1H), 2.11-1.80 (m, 4H), 1.38 (s, 24H).
LC-MS (ESI): [M+H]⁺=413.1

Example 102

N-(3,5-dichloro-2-hydroxyphenyl)-2-(3-methyloxetan-3-yl)acetamide

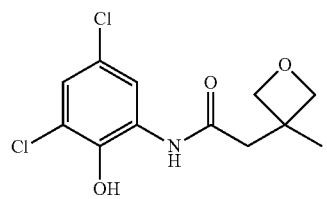 [SMILES: CC1(CC(=O)Nc2cc(Cl)cc(Cl)c2O)COC1]

Example 103

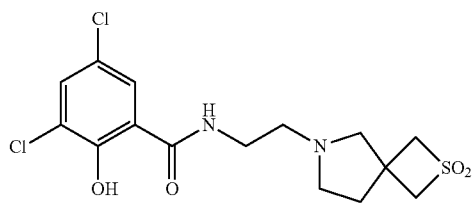 [SMILES: O=C(NCCN1CCC2(C1)CS(=O)(=O)C2)c1cc(Cl)cc(Cl)c1O]

3,5-dichloro-N-(2-(2,2-dioxido-2-thia-6-azaspiro
[3.4]octan-6-yl)ethyl)-2-hydroxybenzamide Example 104

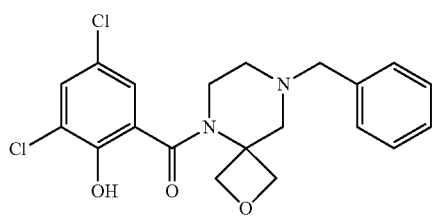 [SMILES: O=C(c1cc(Cl)cc(Cl)c1O)N1CCN(Cc2ccccc2)CC12COC2]

(8-benzyl-2-oxa-5,8-diazaspiro[3.5]nonan-5-yl)(3,5-
dichloro-2-hydroxyphenyl)methanone Example 105

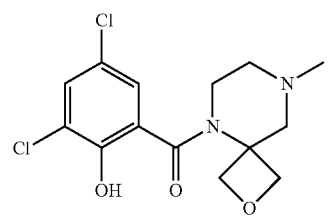 [SMILES: CN1CCN(C(=O)c2cc(Cl)cc(Cl)c2O)C2(COC2)C1]

(3,5-dichloro-2-hydroxyphenyl)(8-methyl-2-oxa-5,8-
diazaspiro[3.5]nonan-5-yl)methanone Example 106

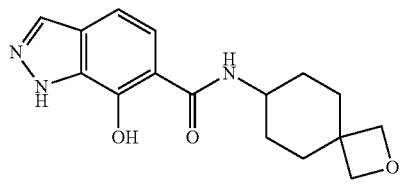 [SMILES: O=C(NC1CCC2(CC1)COC2)c1ccc2cn[nH]c2c1O]

7-hydroxy-N-(2-oxaspiro[3.5]nonan-7-yl)-1H-inda-
zole-6-carboxamide

Example 107

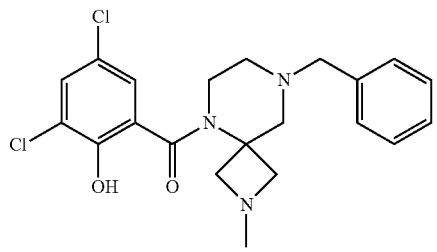 [SMILES: CN1CC2(C1)CN(Cc1ccccc1)CCN2C(=O)c1cc(Cl)cc(Cl)c1O]

(8-benzyl-2-methyl-2,5,8-triazaspiro[3.5]nonan-5-yl)
(3,5-dichloro-2-hydroxyphenyl)methanone Example 108

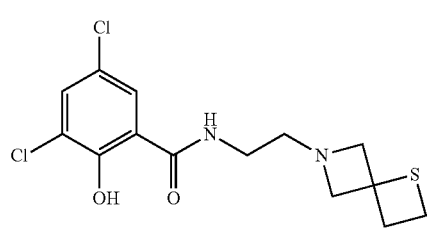 [SMILES: O=C(NCCN1CC2(CCS2)C1)c1cc(Cl)cc(Cl)c1O]

N-(2-(1-thia-6-azaspiro[3.3]heptan-6-yl)ethyl)-3,5-
dichloro-2-hydroxybenzamide

Example 109

3,5-dichloro-N-(2-(1,1-dioxido-1-thia-6-azaspiro
[3.3]heptan-6-yl)ethyl)-2-hydroxybenzamide

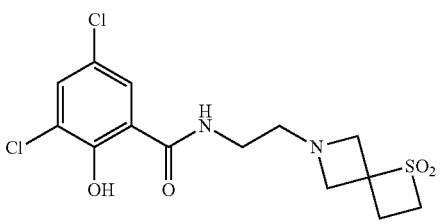 [SMILES: O=C(NCCN1CC2(CCS2(=O)=O)C1)c1cc(Cl)cc(Cl)c1O]

Example 110

N-(3-((2-(cyclopentadecylamino)-3,4-dioxocy-
clobut-1-en-1-yl)amino)-2-hydroxyphenyl)forma-
mide

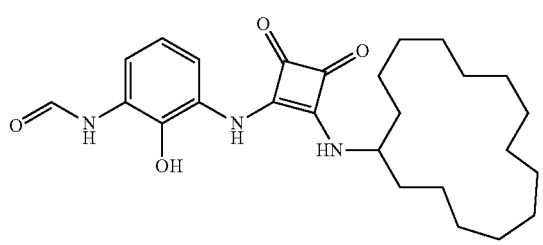 [SMILES: O=CNc1cccc(Nc2c(NC3CCCCCCCCCCCCCC3)c(=O)c2=O)c1O]

Example 111

N-cyclononyl-7-formamido-1H-indole-2-carboxamide

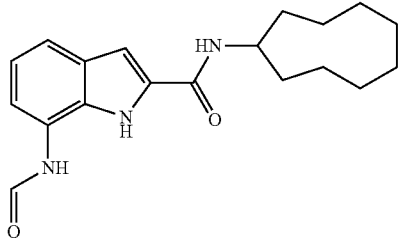 [SMILES: O=CNc1cccc2cc(C(=O)NC3CCCCCCCC3)[nH]c12]

$^1$H NMR (300 MHz, CDCl$_3$) δ 10.15 (s, 1H), 8.80 (d, J=10.4 Hz, 1H), 8.42 (s, 1H), 7.23 (s, 1H), 7.17 (dd, J=8.1, 0.9 Hz, 1H), 6.99 (dd, J=8.1, 7.3 Hz, 1H), 6.65 (dd, J=7.3, 1.0 Hz, 1H), 6.28 (d, J=7.8 Hz, 1H), 4.31-4.10 (m, 1H), 1.96-1.42 (m, 16H).
LC-MS (ESI): [M+H]$^+$=328.2

Example 112

N-cyclononyl-4-(7-formamido-1H-benzo[d]imidazol-2-yl)benzamide

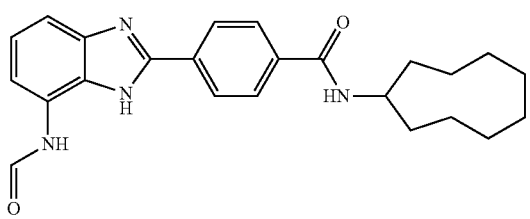 [SMILES: O=CNc1cccc2nc(-c3ccc(C(=O)NC4CCCCCCCC4)cc3)[nH]c12]

$^1$H NMR (300 MHz, Chloroform-d) δ 10.53 (s, 1H), 8.50 (s, 1H), 8.28 (d, J=8.5 Hz, 2H), 8.19 (dd, J=8.3, 0.9 Hz, 1H), 8.10 (d, J=8.6 Hz, 2H), 8.05 (dt, J=8.0, 0.8 Hz, 1H), 7.42 (dd, J=8.0 Hz, 1H), 6.24 (d, J=5.3 Hz, 1H), 4.33-4.19 (m, 1H), 1.86-1.25 (m, 16H).
LC-MS (ESI): [M+H]$^+$=405.2

Example 113

N-cyclononyl-7-hydroxy-1H-indazole-6-carboxamide

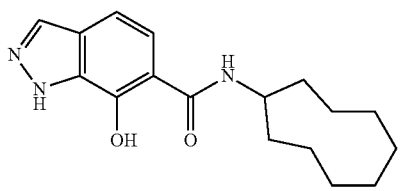 [SMILES: O=C(NC1CCCCCCCC1)c1ccc2cn[nH]c2c1O]

$^1$H NMR (300 MHz, CDCl$_3$) δ 13.66 (s, 1H), 11.32 (s, 1H), 8.06 (s, 1H), 7.18 (d, J=8.6 Hz, 1H), 7.03 (d, J=8.6 Hz, 1H), 6.28 (d, J=8.0 Hz, 1H), 4.30 (dq, J=8.2, 4.1 Hz, 1H), 2.18-1.39 (m, 16H).
LC-MS (ESI): [M+H]$^+$=302.2

Example 114

N-cyclononyl-2-oxo-2,3-dihydro-1H-benzo[d]imidazole-4-carboxamide

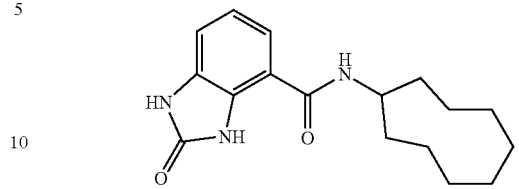

$^1$H NMR (300 MHz, CDCl$_3$) δ 10.20 (s, 1H), 9.59 (s, 1H), 7.21-7.00 (m, 3H), 6.21 (d, J=8.1 Hz, 1H), 4.27 (dp, J=12.0, 4.0 Hz, 1H), 2.09-1.40 (m, 16H).
LC-MS (ESI): [M+H]$^+$=302.2

Example 115

N-cyclopentadecyl-2-oxo-2,3-dihydro-1H-benzo[d]imidazole-4-carboxamide

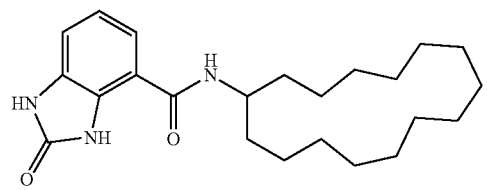 [SMILES: O=C(NC1CCCCCCCCCCCCCC1)c1cccc2[nH]c(=O)[nH]c12]

$^1$H NMR (300 MHz, CDCl$_3$) δ 10.25 (s, 1H), 9.58 (s, 1H), 7.23-6.93 (m, 3H), 6.08 (d, J=8.6 Hz, 1H), 4.31-4.05 (m, 1H), 1.88-1.13 (m, 28H).
LC-MS (ESI): [M+H]$^+$=386.3

Example 116

N-(2-hydroxy-3-(1-(4-(trifluoromethyl)benzyl)-1H-1,2,3-triazol-4-yl)phenyl)formamide

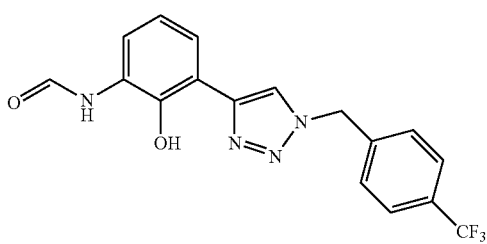 [SMILES: O=CNc1cccc(-c2cn(Cc3ccc(C(F)(F)F)cc3)nn2)c1O]

Example 117

N-adamantan-1-yl-4-((2,5-dihydroxybenzyl)amino)benzamide

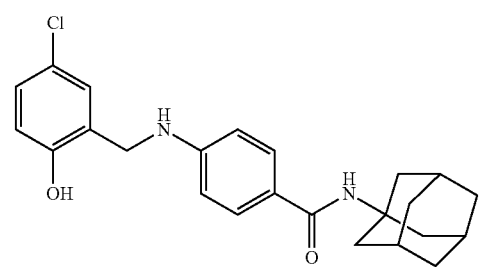 [SMILES: O=C(NC12CC3CC(CC(C3)C1)C2)c1ccc(NCc2cc(Cl)ccc2O)cc1]

¹H NMR (300 MHz, CD₃OD-d₄) δ 7.77-7.70 (m, 1H), 6.74-6.46 (m, 6H), 4.30 (s, 2H), 2.20-2.08 (m, 9H), 1.81-1.62 (m, 6H).
LC-MS (ESI): [M+H]⁺=393.1

Example 118

N-adamantan-1-yl-4-((3,5-dichloro-2-hydroxybenzyl)amino)benzamide

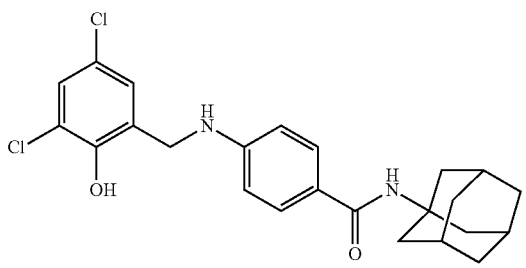 [SMILES: O=C(NC12CC3CC(CC(C3)C1)C2)c1ccc(NCc2cc(Cl)cc(Cl)c2O)cc1]

¹H NMR (300 MHz, DMSO-d₆) δ 9.74 (br s, 1H), 7.53 (d, J=8.4 Hz, 2H), 7.35 (d, J=2.6 Hz, 1H), 7.08 (s, 2H), 6.65 (br s, 1H), 6.49 (d, J=8.4 Hz, 2H), 4.28 (s, 2H), 2.12-1.92 (m, 9H), 1.69-1.54 (m, 6H).
LC-MS (ESI): [M+H]⁺=445.0

Example 119

N-(4-(adamantan-1-ylcarbamoyl)phenyl)-3,5-dichloro-2-hydroxybenzamide

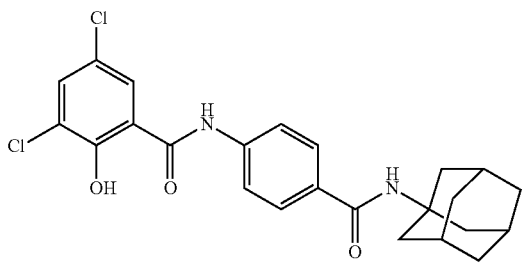 [SMILES: O=C(NC12CC3CC(CC(C3)C1)C2)c1ccc(NC(=O)c2cc(Cl)cc(Cl)c2O)cc1]

¹H NMR (300 MHz, CDCl₃) δ 10.10 (s, 1H), 7.89 (d, J=2.5 Hz, 1H), 7.47 (d, J=8.6 Hz, 2H), 7.43 (d, J=2.2 Hz, 1H), 6.57 (d, J=8.5 Hz, 2H), 5.89 (s, 1H), 5.74 (s, 1H), 2.20-2.08 (m, 9H), 1.81-1.62 (m, 6H).
LC-MS (ESI): [M+H]⁺=459.1

Example 120

N-(4-(adamantan-1-ylcarbamoyl)phenyl)-3-formamido-2-hydroxybenzamide

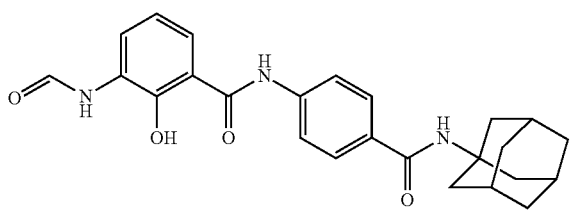 [SMILES: O=CNc1cccc(C(=O)Nc2ccc(C(=O)NC34CC5CC(CC(C5)C3)C4)cc2)c1O]

¹H NMR (300 MHz, CDCl₃) δ 9.42 (s, 1H), 7.71-7.60 (m, 1H), 7.52 (d, J=8.5 Hz, 2H), 7.42-7.21 (m, 3H), 6.61 (d, J=8.5 Hz, 2H), 5.69 (s, 1H), 4.95 (s, 1H), 2.21-2.01 (m, 9H), 1.80-1.60 (m, 6H).
LC-MS (ESI): [M+H]⁺=434.1

Figure 2:
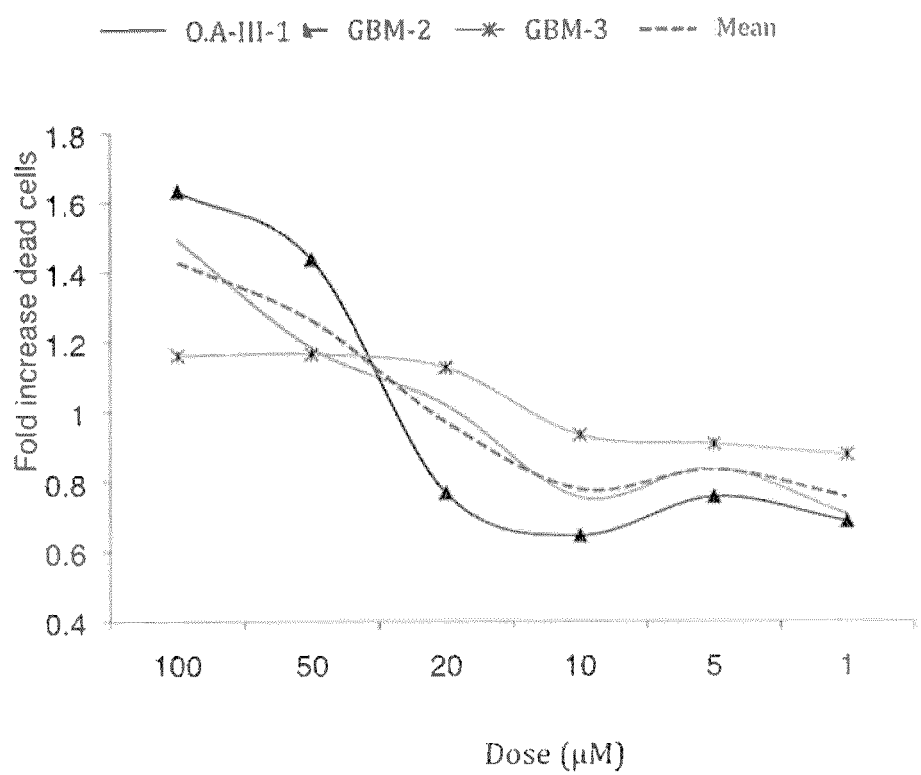
FIG. 2 shows dose response experiment. GICs were exposed to various doses of the compound of Example 92 for 48 hrs. Cell death was measured by incorporating trypan blue and was quantified by Flow cytometry. O.A-III stands for oligoastrocytoma grade III and GBM stands for Glioblastoma Multiforme, -1,-2,-3 represents GBM from various patients
Figure 3:
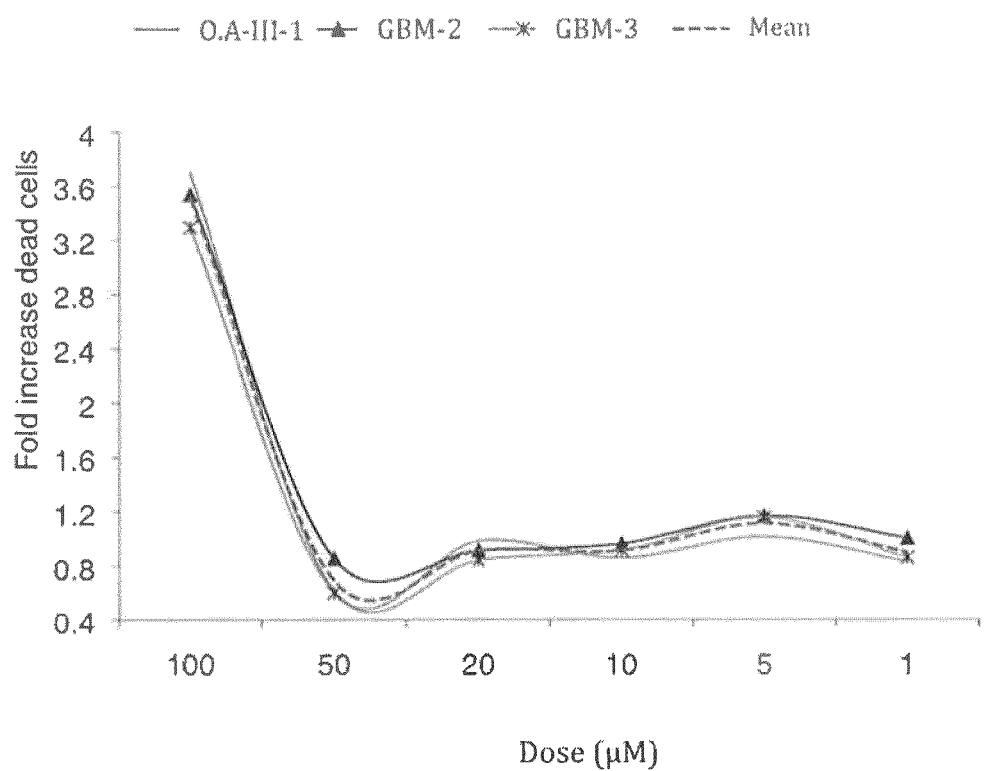
FIG. 3 shows dose response experiment. GICs were exposed to various doses of the compound of the Example 93 for 48 hrs. Cell death was measured by incorporating trypan blue and was quantified by Flow cytometry. O.A-III stands for oligoastrocytoma grade III and GBM stands for Glioblastoma Multiforme, -1,-2,-3 represents GBM from various patients

Biological Test:

The efficacy of a compound in decreasing and/or eradicating the tumor-initiating cells (e.g. recurrence of the cancer initiating cells) was assayed by detecting the presence of initiating cells in a cell sample after treatment (FIGS. 1, 2, 3: 48 hrs treatment) with the compounds according to the present invention, for example by a method as described in PCT/IB2008/054872 and PCT/IB2010/052237, i.e. comprising the following steps:

a) Providing a cancer stem cell sample which was treated by a compound or a method according to the invention;
b) Incubating the treated stem cell sample in a stem cell culture medium for an incubation period without treatment;
c) Selecting the viable cell population from the stem cell sample incubated under step (b);
d) Measuring the mean level of autofluorescence on the viable cell population isolated under step (c) by detecting, by fluorescence activated cell sorting, cells presenting autofluorescence emission in the FL1 channel upon laser beam excitation at a wavelength of or about 488 nm;
e) Isolating cells by fluorescence activated cell sorting cell which have a specific morphology (high FSC and low/middle SSC) and present autofluorescence emission in the FL1 channel upon laser beam excitation at a wavelength of or about 488 nm of the viable cell population isolated under step (c);
f) Isolating cells by fluorescence activated cell sorting which have a specific morphology (low/middle FSC and middle/high SSC), do not present autofluorescence emission in the FL1 channel under step (c) and present a slight positive shift in the cell fluorescence emission in the FL3 and/or FL4 channel upon laser beam excitation of the viable cell population isolated under step (c);
g) Calculating the percentage of autofluorescent viable cells by comparing the mean level of autofluorescence in the cancer stem cell sample provided under step (a) and the mean level of autofluorescence measured under step (d);
h) Calculating the percentage of the cell death by comparing the number of initial cells present in the cancer stem cell sample provided under step (a) and the resulting viable cell population isolated under step (c);
i) Calculating the percentage of viable FL1⁺ cells by comparing the number of initial FL1⁺ cells present in the cancer stem cell sample provided under step (a) and the resulting viable FL1⁺ cell population isolated under step (e);
j) Calculating the percentage of viable FL1⁰ cells by comparing the number of initial FL1⁰ cells present in the cancer stem cell sample provided under step (a) and the resulting viable FL1⁰ cell population isolated under step (f);

Results: see FIGS. 1, 2 and 3.

The invention claimed is:
1. A compound selected from the group consisting of:
 (a) 3-formamido-N-(heptadecan-9-yl)-2-hydroxybenzamide;
 (b) N-cyclopentadecyl-7-hydroxy-1H-indazole-6-carboxamide;
 (c) N-cyclopentadecyl-3-formamido-2-hydroxybenzamide;
 (d) N-cyclododecyl-3-formamido-2-hydroxybenzamide;
 (e) 3, 5-dichloro-N-cyclopentadecyl-2-hydroxybenzamide;
 (f) 3, 5-dichloro-N-decyl-2-hydroxybenzamide;

(g) N-(3, 5-dichloro-2-hydroxyphenyl)undecanamide;
(h) N-(4-(cyclopentadecylcarbamoyl)phenyl)-3-formamido-2-hydroxybenzamide;
(i) N-(heptadecan-9-yl)-2-oxo-2,3-dihydro-1H-benzo[d]imidazole-4-carboxamide;
(j) N-(3-(1-(heptadecan-9-yl)-1H-1,2,3-triazol-4-yl)-2-hydroxyphenyl)formamide;
(k) N-(3-(1-cyclopentadecyl-1H-1,2,3-triazol-4-yl)-2-hydroxyphenyl)formamide;
(l) N-cyclononyl-7-hydroxy-1H-indazole-6-carboxamide;
(m) N-cyclononyl-2-oxo-2,3-dihydro-1H-benzo[d]imidazole-4-carboxamide; and
(n) N-cyclopentadecyl-2-oxo-2, 3-dihydro-1H-benzo[d]imidazole-4-carboxamide, or a pharmaceutically acceptable salt or solvate of any one of (a)-(n).

2. The compound of claim 1, selected from the group consisting of (a)-(e)
(a) 3-formamido-N-(heptadecan-9-yl)-2-hydroxybenzamide;
(b) N-cyclopentadecyl-7-hydroxy-1H-indazole-6-carboxamide;
(c) N-cyclopentadecyl-3-formamido-2-hydroxybenzamide;
(d) N-cyclododecyl-3-formamido-2-hydroxybenzamide; and
(e) 3, 5-dichloro-N-cyclopentadecyl-2-hydroxybenzamide, or a pharmaceutically acceptable salt or solvate of any one of (a)-(e).

3. The compound of claim 2, selected from the group consisting of:
(a) 3-formamido-N-(heptadecan-9-yl)-2-hydroxybenzamide; and
(b) N-cyclopentadecyl-7-hydroxy-1H-indazole-6-carboxamide, or a pharmaceutically acceptable salt or solvate of (a) or (b).

4. A method for treating a cancer presenting tumor-initiating cells, the method comprising administering a compound, salt, or solvate of claim 1 to a patient in need thereof.

5. The method according to claim 4, wherein the cancer presenting tumor-initiating cells is selected from the group consisting of human glioma, schwannoma, metastasis to the brain, meningioma, ependymoma, and a metastatic cancer.

6. The method according to claim 5, wherein the metastatic cancer is selected from the group consisting of melanoma, breast cancer, colon cancer, and lung cancer.

7. A pharmaceutical composition comprising a pharmaceutically acceptable carrier and a therapeutically effective amount of the compound, salt, or solvate according to claim 1.

8. A kit comprising the compound, salt, or solvate according to claim 1.

9. The kit according to claim 8, further comprising one or more chemotherapeutic agent selected from the group consisting of Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide, Tioguanine/Thioguanine, Thiotepa, Topotecan, Treosulfan, Vinblastine, Vincristine, Vindesine, and Vinorelbine.

10. A kit comprising the pharmaceutical composition according to claim 7.

11. The kit according to claim 10, further comprising one or more chemotherapeutic agent selected from the group consisting of Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide, Tioguanine/Thioguanine, Thiotepa, Topotecan, Treosulfan, Vinblastine, Vincristine, Vindesine, and Vinorelbine.

12. A method of achieving an antibacterial effect, an antifungal effect, a pesticidal effect and/or a herbicidal effect, the method comprising administering an effective dose of a compound, salt, or solvate according to claim 1 to an infection or infestation.

13. The compound of claim 1, wherein the compound is N-cyclopentadecyl-3-formamido-2-hydroxybenzamide, or a pharmaceutically acceptable salt or solvate thereof.

* * * * *